(12) United States Patent
Siegenthaler

(10) Patent No.: US 9,744,281 B2
(45) Date of Patent: *Aug. 29, 2017

(54) CATHETER-BASED HEART SUPPORT SYSTEM AND METHOD OF IMPLANTING THEREOF

(71) Applicant: Michael Siegenthaler, Potomac, MD (US)

(72) Inventor: Michael Siegenthaler, Potomac, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/991,365

(22) Filed: Jan. 8, 2016

(65) Prior Publication Data

US 2016/0199555 A1    Jul. 14, 2016

Related U.S. Application Data

(63) Continuation of application No. 14/888,481, filed as application No. PCT/US2014/036018 on Apr. 30, 2014.

(30) Foreign Application Priority Data

May 2, 2013   (DE) .................. 10 2013 208 038

(51) Int. Cl.
*A61M 1/12*    (2006.01)
*A61M 1/10*    (2006.01)
(Continued)

(52) U.S. Cl.
CPC ............... *A61M 1/122* (2014.02); *A61F 2/24* (2013.01); *A61M 1/1024* (2014.02);
(Continued)

(58) Field of Classification Search
CPC .... A61M 1/10; A61M 1/1001; A61M 1/1008; A61M 1/101; A61M 1/1012;
(Continued)

(56) References Cited

U.S. PATENT DOCUMENTS

| | | | | |
|---|---|---|---|---|
| 4,753,221 A | * | 6/1988 | Kensey ................. | A61M 1/101 415/221 |
| 5,169,378 A | | 12/1992 | Figuera | |

(Continued)

FOREIGN PATENT DOCUMENTS

| | | |
|---|---|---|
| CN | 1274293 | 11/2000 |
| CN | 102821797 | 12/2012 |

(Continued)

OTHER PUBLICATIONS

Pubmed author search: "Siegenthaler MP". <https://www.ncbi.nlm.nih.gov/pubmed/?term=Siegenthaler+MP%5BAuthor%5D>. Accessed Nov. 10, 2016*

(Continued)

*Primary Examiner* — Eugene T Wu
(74) *Attorney, Agent, or Firm* — Bond, Schoeneck & King, PLLC; William Greener

(57) ABSTRACT

The invention relates to a device for circulatory support of the heart and to a corresponding method with a holding means which is configured such that it can be implanted intracardially in the left and/or right ventricular outflow tract of the heart by means of a catheter, preferably using an endovascular method, through a femoral access and/or a percutaneous transventricular, transseptal, transapical or transvenous access, wherein the holding means comprises an anchoring means which can be fixed in the subcommissural triangle underneath the aortic valve and the pulmonary valve, respectively in the flow direction of the blood on the ventricular side of the aortic valve and the pulmonary valve, respectively, a pump which is configured such that it can be fixed in the holding means by means of a catheter, preferably using an endovascular method, through a femoral access and/or a percutaneous transventricular, transseptal, transapical or transvenous access, wherein the pump (a) can either be inserted releasably into the holding means after the (Continued)

holding means has been fixed by means of the anchoring means in the subcommissural triangles underneath the aortic valve and the pulmonary valve, respectively or (b) is firmly connected to the collapsible and expandable anchoring means.

6 Claims, 20 Drawing Sheets

(51) Int. Cl.
    *A61F 2/24*         (2006.01)
    *A61N 1/05*         (2006.01)
    *A61F 2/07*         (2013.01)
    *A61F 2/82*         (2013.01)

(52) U.S. Cl.
    CPC ........ *A61M 1/1036* (2014.02); *A61M 1/1049* (2014.02); *A61M 1/125* (2014.02); *A61N 1/057* (2013.01); *A61F 2/07* (2013.01); *A61F 2/82* (2013.01); *A61M 1/127* (2013.01)

(58) Field of Classification Search
    CPC .............. A61M 1/1013; A61M 1/1015; A61M 1/1024; A61M 1/1036; A61M 1/122; A61M 1/125

See application file for complete search history.

(56) References Cited

U.S. PATENT DOCUMENTS

| | | | |
|---|---|---|---|
| 5,290,227 A | 3/1994 | Pasque | |
| 8,690,749 B1* | 4/2014 | Nunez | A61M 1/125 |
| | | | 600/16 |
| 8,721,517 B2* | 5/2014 | Zeng | A61M 1/101 |
| | | | 600/19 |
| 8,814,933 B2* | 8/2014 | Siess | A61M 1/101 |
| | | | 623/3.13 |
| 9,364,593 B2* | 6/2016 | McBride | A61M 1/101 |
| 2003/0135086 A1 | 7/2003 | Khaw et al. | |
| 2006/0195004 A1* | 8/2006 | Jarvik | A61M 1/12 |
| | | | 600/16 |
| 2008/0004485 A1 | 1/2008 | Moreschi | |
| 2009/0112312 A1* | 4/2009 | LaRose | A61M 1/101 |
| | | | 623/3.13 |
| 2010/0249489 A1* | 9/2010 | Jarvik | A61F 2/2412 |
| | | | 600/16 |
| 2011/0152999 A1* | 6/2011 | Hastings | A61M 1/101 |
| | | | 623/1.15 |
| 2011/0238088 A1 | 9/2011 | Bolduc et al. | |
| 2012/0059460 A1 | 3/2012 | Reitan | |
| 2012/0143324 A1* | 6/2012 | Rankin | A61F 2/2418 |
| | | | 623/2.37 |
| 2013/0066421 A1 | 3/2013 | Strueber et al. | |
| 2014/0128967 A1* | 5/2014 | Jarvik | A61F 2/2418 |
| | | | 623/2.17 |
| 2015/0038770 A1 | 2/2015 | Colella | |

FOREIGN PATENT DOCUMENTS

| | | |
|---|---|---|
| EP | 2233169 | 9/2010 |
| WO | 2012047761 | 4/2012 |

OTHER PUBLICATIONS

Siegenthaler et al. "Endovascular treatment for thoracoabdominal aneurysms: outcomes and results". European Journal of Cardio-thoracic Surgery 34 (2008) 810-819.*
International Search Report and Written Opinion Form PCT/ISA/220, International Application No. PCT/US2014/036018, pp. 1-15, International Filing Date Apr. 30, 2014.

* cited by examiner

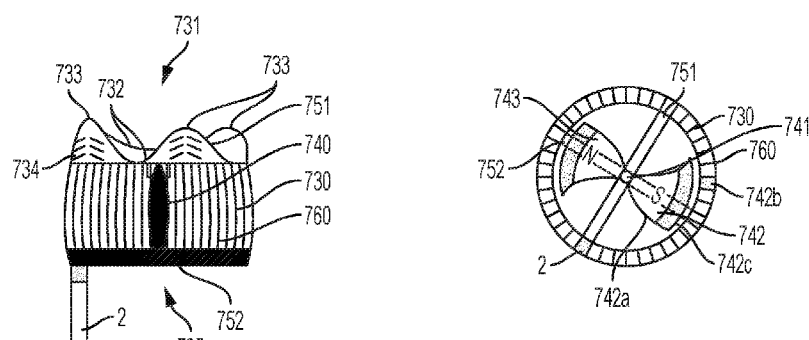
FIG. 10A
FIG. 10B
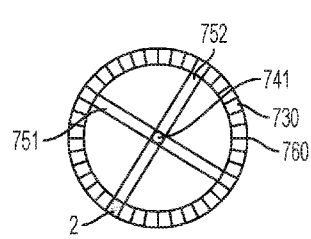
FIG. 10C
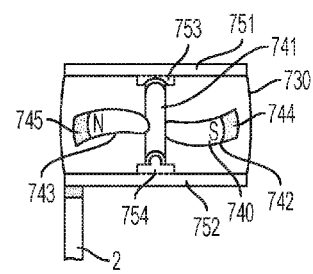
FIG. 10D
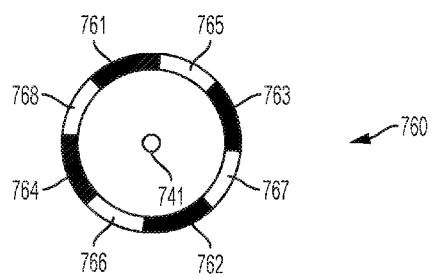
FIG. 10E

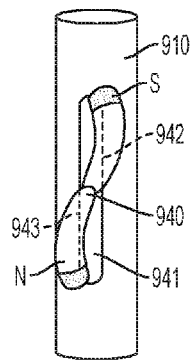 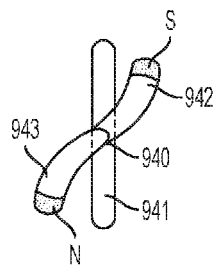 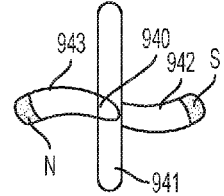
FIG. 11A  FIG. 11B  FIG. 11C
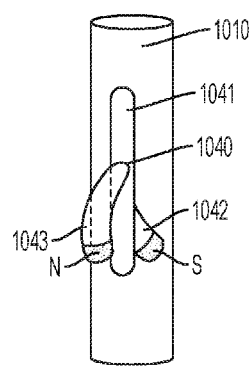 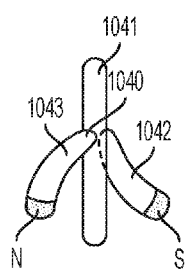 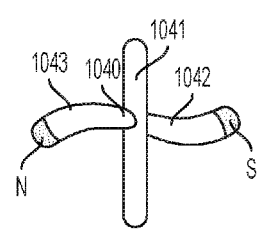
FIG. 12A  FIG. 12B  FIG. 12C

CATHETER-BASED HEART SUPPORT SYSTEM AND METHOD OF IMPLANTING THEREOF

RELATED APPLICATION DATA

The instant application is a continuation (CON) of U.S. application Ser. No. 14/888481 filed Nov. 2, 2015, which was a 35 USC 371 national phase application of PCT/US2014/36018 filed 30 Apr. 2014, which claims priority to DE Application No. 102013208038.7 filed May 2, 2013, and claims priority thereto.

The invention relates to a catheter-based heart support system or catheter-based heart assist system and in particular, to a device for circulatory support of the heart, an electrical supply line or drive line for said device and a system for handling said device and a method of implanting the system in the heart and a method for handling and for adjusting the position of the system.

US 2010/0249489 A1 describes an intraventricular blood pump which can be anchored in the aorta by a fixing means and can project into the left ventricle of the heart of a patient, wherein, the fixing means is fixed in the direction of blood flow in the aorta (i.e. not in the heart, on the aortic side of the aortic valve). The pump is "hung" on the fixing means, wherein the outlet opening is arranged closely adjacent to and above the aortic valve and the fixing means projects through the aortic valve when said pump is implanted. In a further embodiment, the fixing means comprises an expandable stent, which can be fixed above the aortic valve in the flow direction of the blood downstream of the aortic valve. In a further embodiment, a valve prosthesis is arranged at the fixing means, wherein, when the pump is implanted, one end of said valve prosthesis is connected to the outlet opening of the pump and the other end of said valve prosthesis ends in the aorta spaced from the aortic valve. US 2010/0249489 A1 suggests to implant said pump using non-invasive surgery, wherein the pump can be inserted through an opening at the apex of the left ventricle of the heart by means of a catheter. An electrical supply line, which is connected to the pump, is guided through this opening to the outside of the body of a patient. As an alternative, it is suggested that the electrical supply line is guided to the outside via the aorta, wherein in said case the pump should be inserted by means of a catheter system through the aorta.

US 2006/0195004 A1 relates to a blood pump which can be implanted in the area of the aortic valve of the heart of a patient, wherein a part of the device should be supported in the outflow tract of the ventricular space adjacent to the aortic valve. In the implanted state, two of the three aortic valve leaflets should retain their natural function, while the pump is arranged in the area of the third aortic valve leaflet.

It is an object of the present invention to provide a device for circulatory support of the heart as well as an electrical supply line for said device and a system for handling said device and a method of implanting the system in the heart and a method for handling and for adjusting the position of the system.

This object is achieved by the features of the independent claims. The dependent claims relate to preferred embodiments of the invention.

The present invention starts out from the basic idea to provide a device which comprises a pump and a holding means and is configured and structured such that it can be implanted in the left or right ventricular outflow tract of the heart. Furthermore, this device can be implanted in the left or right ventricular outflow tract of the heart in such a manner that the heart retains its natural function and is not adversely affected by the device when the device is implanted.

In accordance with an aspect of the invention, the device for circulatory support of the heart comprises a holding means which is configured such that it can be implanted intracardially in the outflow tract of the left and/or right ventricle of the heart by means of a catheter. Thus, one device can be implanted in either one of the left or right ventricle or two devices can be implanted, one in the left ventricle and another one in the right ventricle. The device and/or the holding means is preferably configured such that it can be implanted in the left or right ventricular outflow tract of the heart by means of a catheter, using an endovascular method, through a femoral access or through a percutaneous transapical access or a combination of both accesses. According to a further aspect the holding means is configured such that it can be implanted in the sub-valvular position of the outlet valve of the respective ventricle, just underneath the aortic or pulmonary valve on the ventricular side.

In accordance with an aspect of the invention, the device for circulatory support of the heart comprises a holding means which is configured such that it can be implanted in the left ventricular outflow tract of the heart by means of a catheter. The holding means is preferably configured such that it can be implanted in the left ventricular outflow tract of the heart by means of a catheter, using an endovascular method, through a femoral access or through a percutaneous transapical access or a combination of both accesses. The holding means comprises anchoring means which can be fixed in the subcommissural triangle underneath the aortic valve in the flow direction of the blood on the ventricular side of the aortic valve.

In accordance with another aspect of the invention, the device for circulatory support of the heart comprises a holding means which is configured such that it can be implanted in the right ventricular outflow tract of the heart by means of a catheter. The holding means is preferably configured such that it can be implanted in the right ventricular outflow tract of the heart by means of a catheter, using an endovascular method, through a femoral access or through a percutaneous transapical access or a combination of both accesses. The holding means comprises anchoring means which can be fixed in the subcommissural triangle underneath the pulmonary valve in the flow direction of the blood on the ventricular side of the pulmonary valve.

In the following description reference is made to implanting the device in either the left or the right ventricle. The description with reference to the left ventricle similarly applies to the case where the device is implanted in the right ventricle and vice versa.

The device for circulatory support of the heart moreover comprises a pump which is configured such that it can be fixed in the holding means by means of a catheter. The pump is preferably configured such that it can be fixed in the holding means by means of the catheter, using an endovascular method, through a femoral access and/or through a percutaneous transapical access.

According to a further aspect of the invention, the pump and the holding means are configured such that the pump can be inserted releasably in the holding means after the holding means has been fixed by the anchoring means in the subcommissural triangles underneath the aortic valve.

According to an alternative aspect of the invention, the pump and the holding means are configured such that the pump is firmly arranged in the holding means and they can be implanted together by means of a catheter in the left or right ventricular outflow tract of the heart, wherein the holding means can be fixed by the anchoring means in the subcommissural triangle underneath the aortic valve in the flow direction of the blood upstream of the aortic valve.

According to a further aspect of the invention, the holding means and/or the anchoring means is/are collapsible so that it/they can be implanted by means of the catheter. More preferably, the holding means and/or the anchoring means is/are expandable, preferably self-expandable, so that the anchoring means can be anchored in the subcommissural triangle underneath the aortic valve.

According to a further aspect of the invention, the anchoring means comprises at least one expandable stent, which can be expanded by means of a balloon or which is preferably configured such that it generates a self-expanding force which can cause anchorage in the fibrous tissue in the subcommissural triangles of the left or right heart ventricle. Preferably, the expandable stent has at least one hook by means of which the stent causes anchorage in the fibrous tissue in the subcommissural triangles of the left or right heart ventricle.

According to another aspect of the invention, the pump comprises an electric motor and a blade connectable thereto, wherein in the implanted state of the pump, the motor rotates the blade such that blood can be pumped from the left heart ventricle in the direction of the aortic valve or from the right heart ventricle in the direction of the pulmonary valve.

According to a further aspect of the invention, the electric motor comprises first means forming the stator and being arranged at the stent and second means forming the rotor and being arranged centrally inside the first means, wherein the first means are collapsible and expandable.

Preferably, the first means form the stator coils of the electric motor. Also preferably, the second means form the rotor with permanent magnets of the electric motor.

According to a further aspect of the invention, the first means comprise electrical coils and the second means of the electric motor comprise permanent magnets. Alternatively, the first means comprise permanent magnets and the second means of the electric motor comprise electrical coils. The electrical coils can be connected to a power supply apparatus by means of a supply line.

According to an alternative aspect of the invention, the pump comprises an electric motor comprising flexible suspension means which are collapsible for implantation and by means of which the electric motor can be releasably inserted at the anchoring means, preferably the stent. The electric motor can be connected to a power supply apparatus by means of a supply line.

According to a further alternative embodiment, the pump comprises a rotational shaft at which at least one blade is arranged, wherein the blade is collapsible for implanting the pump and configured such that it is rotatable with the rotational shaft in the mounted state of the pump and automatically straightens up and/or can be straightened up in an operating position, and during operation of the pump blood can be pumped in the direction of the aortic valve.

According to a further embodiment, the pump is a rotary blood pump, preferably an axial flow pump or a centrifugal pump. The rotary blood pump is firmly arranged in the holding means. The rotary blood pump is preferably attached to the anchoring means or anchoring stent which is arranged on the ventricular side of the aortic valve in the left ventricular outflow tract or the ventricular side of the pulmonary valve in the right ventricular outflow tract. The rotary blood pump pumps the blood from the left ventricle across the aortic valve in the systemic circulation, when implanted in the left ventricle. Similarly, the rotary blood pump pumps the blood from the right ventricle across the pulmonary valve in the pulmonary circulation, when implanted in the right ventricle.

According to an aspect of the invention, an electrical supply line is configured such that it connects the circulatory support device, which can be implanted in the left ventricular outflow tract of the heart, to a power source and/or a control apparatus. The electrical supply line is preferably configured such that it can be pulled out of the heart by means of a guide wire and can seal the opening in the heart for the percutaneously placed guide wire.

According to an aspect of the invention, the electrical supply line is configured such that it can be guided from the left ventricle of the heart through the apex of the left ventricle of the heart and preferably further to a site at the skin surface of a patient.

According to an alternative embodiment, the electrical supply line is configured such that it can be guided from the left ventricle of the heart through the lateral wall of the left ventricle or through the lower wall of the left ventricle and preferably further to a site at the skin surface of a patient.

According to a further embodiment, the electrical supply line is configured such that it extends in the cardiac septum up to the apex of the heart or to the front or the rear outer wall of the septum and can preferably be guided further to a site at the skin surface of a patient.

According to yet a further embodiment of the invention, the electrical supply line is configured such that it can be guided from the left ventricle of the heart through the cardiac septum in the right ventricle and then further through the free wall of the right ventricle and preferably further to a site at the skin surface of a patient.

According to yet a further embodiment of the invention, the electrical supply line is configured such that it can be guided from the left ventricle of the heart through the cardiac septum into the right ventricle and then further into the right atrium, then transvenously via a large vena cava out of a large peripheral vein (e.g. subclavian vein, jugular vein, axillary or femoral vein) preferably further to a site at the skin surface of a patient.

According to yet a further embodiment of the invention, the electrical supply line is configured such that it can be guided from the left ventricle of the heart to the left atrium through the interatrial septum into the right atrium, then transvenously via a large vena cava out of a large peripheral vein (e.g. subclavian vein, jugular vein, axillary or femoral veins) preferably further to a site at the skin surface of a patient.

An aspect of the invention relates to a system for handling the device for circulatory support of the heart and the supply line, in particular for implanting the device and the supply line and/or for removing the device and the supply line and/or for newly positioning or adjusting the device and the supply line. The system preferably comprises a catheter means for implanting the device and for newly positioning or adjusting the device in the left ventricle of the heart of a patient.

According to an aspect of the invention, the second catheter means comprises a guide wire which is configured such that it can be used for pulling the supply line out of the heart, wherein the electrical supply line seals the opening in the heart of the preferably percutaneously placed guide wire.

According to an aspect of the invention, the preferably percutaneously placed guide wire is configured such that it can be used for pulling the electrical supply line through the apex or the lateral or lower wall of the left ventricle out of the heart, and the opening for the percutaneously placed guide wire can be sealed.

According to a further aspect of the invention, the preferably percutaneously placed guide wire is configured such that it can be used for pulling the electrical supply line in the cardiac septum out of the heart, and the opening for the percutaneously placed guide wire can be sealed.

According to a further alternative embodiment, the preferably percutaneously placed guide wire is configured such that the electrical supply line can be pulled through the cardiac septum into the right ventricle and then through the free wall of the right ventricle out of the heart, and the opening for the percutaneously placed guide wire can be sealed.

According to a further alternative embodiment, the preferably percutaneously placed guide wire is configured such that the electrical supply line can be pulled through the cardiac septum into the right ventricle and then through the right atrium transvenously via the large vena cava out of a large peripheral vein (e.g. the subclavian vein, jugular vein, axillary or femoral veins), and the opening for the percutaneously placed guide wire can be sealed.

According to a further alternative embodiment, the preferably percutaneously placed guide wire is configured such that the electrical supply line can be pulled from the left ventricle to the left atrium through the atrial septum into the right atrium transvenously via a large vena cava out of a large peripheral vein (e.g. subclavian vein, jugular vein, axillary or femoral veins), and the opening for the percutaneously placed guide wire can be sealed.

In accordance with a further aspect of the invention, a connector is described, in particular a plug-in connector for an electrical supply line. The connector is configured for being arranged in the subcutaneous tissue of a patient and for providing a releasable electrical connection between an implanted part of an electrical supply line and a part of the electrical supply line being directed outwardly.

The connector is preferably provided in the subcutaneous tissue. In case of an infection or would healing disorder at the exit site of the control line, it is thus not necessary to replace the entire system but it is sufficient to provide a new control line and connect it by means of the new subcutaneous plug-in connector to the heart support system. Upcoming infections can thus be prevented.

Application in the subcommissural triangle has considerable advantages vis-à-vis the prior art. On the one hand, in this position no inlet cannula of the heart support system is necessary. In accordance with the present prior art, inlet cannulae are associated with most of the thrombo-embolic complications. Because of its position, the present invention does not need an inlet port and is advantageous in that the blood on the inlet side of the pump does not come in contact with a foreign surface or only to a much lesser extent than in conventional heart support systems.

The attachment below the aortic valve and pulmonary valve, respectively has not yet been described in the prior art because the anatomical anchoring of a stent in this position is difficult to imagine to a non-heart surgeon and requires an exact knowledge of the anatomy of the heart. This fixing method has not yet been taken into consideration.

It is a disadvantage of systems, which pump the blood within the arterial system that, starting from a certain pumping power on the side of the inlet cannula, where the blood is sucked, a "steal phenomenon" appears. The latter is caused in that a negative or reduced arterial pressure is created at the inlet cannula, which can reduce the blood flow to arterial side branches in the area of the inlet cannula. A reduced coronary flow occurs in the ascending aorta starting from a certain flow rate, which might cause a coronary ischemia with all possible consequences such as arrhythmia, deterioration of the diastolic and systolic heart insufficiency and myocardial infarction. When being positioned downstream of the head vessels, such a configuration can additionally also cause a cerebral ischemia. When arranging the heart support system below the aortic valve in accordance with the present invention, such a "steal phenomenon" is prevented because the coronaries, the first branches of the arterial system, lie directly above the aortic valve, i.e. in the outflow tract of the heart assist system. As the pumping power increases, there is only an increased emptying of the left or right heart ventricle and an increased blood flow in the arterial system.

Systems traversing the aortic valve are disadvantageous in that either a biological valve is required or a foreign body comes in contact with the aortic valve at any heart cycle, which in the long term might lead to a valve degeneration. Biological valves used in heart support systems have a relatively short lifetime and, e.g., in the rematch trial had been one of the main reasons, which led to a failure of the device in the Heartmate system after one to two years. The present invention is advantageous in that the native aortic valve of the patient is left untouched, is not always exposed to mechanical forces, which are normally not present, and can continue its function. There are no biological or artificial valves, which combine all advantages of a native heart valve.

The optional collapsible embodiment of the present invention also requires larger distances between the rotor and the stator than conventional rotary blood pumps. This necessarily leads to a less efficient pump, which despite rotor optimization cannot overcome a systematic pressure gradient. Such a pump configuration thus is even more sensitive to afterload than the systems nowadays used. Only by providing the pump on the ventricular side of the aortic valve can such a pump configuration function. With a pressure gradient of 20 mm Hg, the present invention can pump about 20 liters per minute, which means that in a heart support system of the heart, about 6 liters per minute are pumped during the systole, which is sufficient for a cardiac assist device.

Our invention also allows to anchor a conventional small rotary blood pump, preferably an axial flow pump or a centrifugal flow pump by means of the stent in the left ventricular outflow tract or in the right ventricular outflow tract, more specifically to anchor the stent in the fibrous tissue in the subcommissural triangles adjacent to the aortic or pulmonary valve.

It is a further advantage that in case of an interruption of the operation of the system, the physiology of an acute massive aortic valve insufficiency does not occur. Today's heart support systems are disadvantageous in that in case of power interruptions, which occur in almost all patients using heart support systems for a long time, can lead to an acute massive deterioration.

Furthermore, the device of the present invention is positioned in a zone of the heart which has relatively little stasis of the blood, contrary to the apex of the ventricle and the atrium. It is therefore conceivable that this configuration is less sensitive to thrombo-embolic complications because of the high wash-out of the system.

The holding means of the present invention extends into the left (or right) ventricular outflow tract. This has the advantage that in addition to the anchoring directly under the aortic valve, it keeps the blood flow to the device open and prevents collapse and sucking-in of intraventricular structures and sucking-in of the front mitral valve leaflet (or tricuspid valve). The holding means is implanted into the left ventricular outflow tract, where it has no anchoring function but guarantees the flow to the rotor. Even at a physiological pumping power of 4 to 5 liters per minute, the front leaflet of the mitral valve will not be sucked into the left ventricular outflow tract and will not have a negative effect on the emptying of the ventricle and the function of the pump.

The described electrical line, which is guided via a guide wire and seals the apex of the heart, is advantageous in that it does not require a surgical access.

One further aspect of the invention relates to a minimally invasive method to implant a left and/or right ventricular assist device in a sub-valvular position of the outlet valve of the respective ventricle, i.e. just underneath the aortic or pulmonary valve using holding means, preferably a stented anchoring device (as shown for example in FIG. 1). The holding means holds a preferentially rotary blood pump in position to allow circulatory support of the heart. The method entails inserting a relatively large device through a large artery or vein or directly though the heart and bringing it to the sub-valvular position of the heart for circulatory support.

A further aspect of the invention relates to a method of assist device implantation of said device using endovascular over-the-wire techniques. It entails access to the vascular system or directly the heart at one or two separate points to allow control of a guide wire at both ends ("tooth-floss technique", see for example FIG. 9), which allows precise device control for exact deployment at the desired landing point in the sub-valvular position.

This method also entails adjusting and correcting of the device position with traction on the wires in opposite directions, if needed. Traction on both ends of the wires allows partial collapse of the device (see for example FIG. 17).

Still another aspect of the invention relates to a method that entails sealing and hemostasis of the access puncture site of the heart or vascular system after device deployment. The sealing and hemostasis is accomplished with a driveline, which has a larger diameter than the access catheter used for the procedure. This driveline serves to seal the access site and is pulled out over a wire and will subsequently seal the vascular/cardiac access site. This method preferably uses a driveline that has one or more longitudinal wire channels. The driveline preferably has a configuration with a diameter that is designed in such a fashion, that bleeding at the puncture site is prevented by pulling the driveline outside the puncture site in the heart or a blood vessel over the guide wire. The driveline preferably comprises a surface coating that prevents bleeding at the puncture site.

BRIEF DESCRIPTION OF THE DRAWINGS

In the following, the invention will be explained in more detail on the basis of embodiments and the drawings, wherein:

FIG. 10*a* shows a side view of a ninth embodiment of the device according to the invention, FIG. 10*b* shows a top view of the ninth embodiment with built-in rotor, FIG. 10*c* shows a top view of the ninth embodiment of FIG. 10*b* without rotor, FIG. 10*d* shows a detailed view of the ninth embodiment of FIG. 10*a*, wherein a part of the holding means has been omitted, FIG. 10*e* shows a schematic top view of a stator which is integrated in the ninth embodiment, FIGS. 11*a*, 11*b* and 11*c* show schematic views of a first embodiment of a rotor with foldable rotor blades, wherein FIG. 11*a* shows the rotor in a flexible tubular insertion instrument, FIG. 11*b* shows the rotor in the semi-unfolded state of the rotor blade, and FIG. 11*c* shows the rotor with completely unfolded rotor blades, FIGS. 12*a*, 12*b* and 12*c* show schematic views of a second embodiment of a rotor with foldable rotor blades, wherein FIG. 12*a* shows the rotor in a flexible tubular insertion instrument, FIG. 12*b* shows the rotor in the semi-unfolded state of the rotor blade, and FIG. 12*c* shows the rotor with completely unfolded rotor blades.

DETAILED DESCRIPTION

Figure 1:
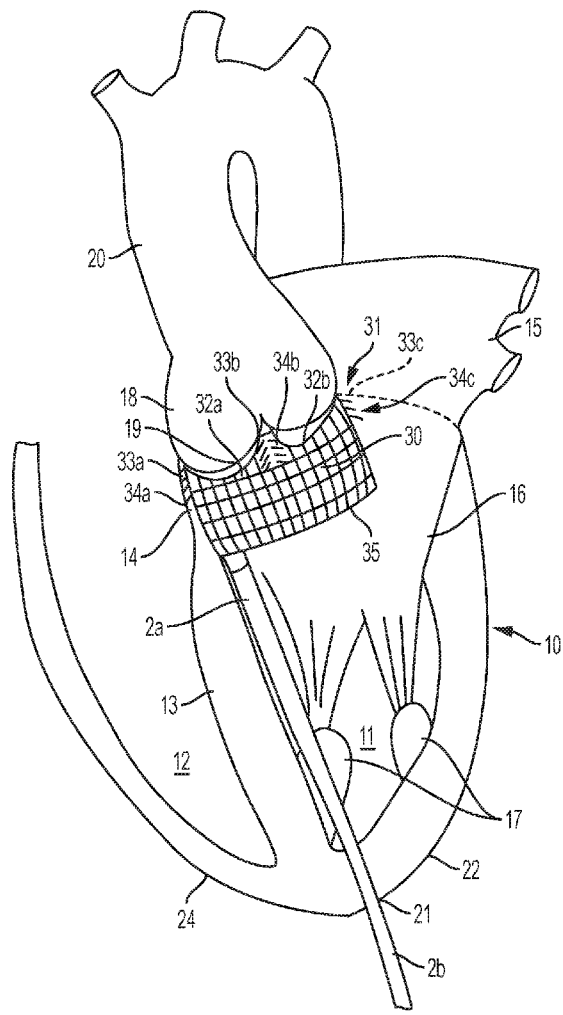
FIG. 1 shows a schematic view of a first embodiment of the invention, which is arranged in the left ventricular outflow tract of the heart and wherein the device is anchored in the subcommissural triangles.

FIG. 1 shows a schematic view of a first embodiment of a device according to the invention, said device being arranged in the left ventricular outflow tract of the heart. The schematic view shows a part of the heart 10 of a patient, wherein the device is arranged therein and anchored in the subcommissural triangles. The left ventricle 11, the right ventricle 12, the muscular septum 13 and the membranous septum 14 are shown. The left atrium 15, the mitral valve 16 and the papillary muscles 17 are also shown. Approximately in the middle of FIG. 1, the root of the aorta 18 is schematically shown together with the aortic valve leaflet 19. Due to the natural pumping activity of the heart, blood is pumped from the left ventricle 11 through the root of the aorta 18 into the aorta, of which aorta ascendens 20 is shown. From there, the blood is further distributed into the different areas of the patient. As schematically shown in FIG. 1, the embodiment of a device for circulatory support of the heart 1 according to the invention is arranged in the left ventricle, more exactly in the left ventricular outflow tract. The device 1 can be connected by means of an electric supply line 2 with an exterior device such as a power supply or control apparatus (not shown). FIG. 1 shows the exterior view of the holding means 30 of the device 1, wherein in accordance with the present embodiment, said holding means 30 comprises a cylindrical metal frame. The metal frame 30 is preferably realized as a so-called stent graft, which is configured in such a manner and made from such a material that the stent graft is collapsible, i.e. can be compressed to a relatively small diameter and can be implanted by means of a catheter device. The stent graft can be expanded after implantation, for example by means of a balloon catheter, or it is self-expandable on account of the structure and design of the stent graft. Nitinol is preferably used as the material for the metal frame or stent graft. FIG. 1 schematically shows the metal frame as a mesh structure which, in accordance with the present example, comprises six wires which are substantially arranged in a circle and connected to a plurality of elongate wires arranged perpendicularly thereto. The shown mesh structure is only exemplary and can have different structures in which the wires are arranged in different manners for providing the desired collapsibility and expandability. This metal frame is preferably produced as one piece.

As schematically shown in FIG. 1, the metal frame has a first end 31 and a second end 35.

The first end 31 of the metal frame is arranged adjacent to the root of the aorta 18 and has a shape that is adapted to the anatomy of the root of the aorta 18. Preferably, this shape can be adapted individually to the shape and size of the individual parts of the root of the aorta of a patient. In the present example, the edge of the first end 31 has three concave recesses, wherein only two of these recesses 32a, 32b are shown in this view. In the area of the recesses, the mesh frame 30 has a shorter length. Between two recesses, a respective projection 33a, 33b, 33c is formed. In the area of each projection, the metal frame has a length that is longer than the length in the area of the recesses. This design including the concave recesses and the projections lying therebetween makes sure that the metal frame follows the anatomic shape of the area adjoining the root of the aorta. In this area adjoining the root of the aorta, the metal frame is anchored.

In the example shown in FIG. 1, hooks 34a, 34b, 34c are arranged at each of the projections 33a, 33b, 33c. There might be one respective hook per projection or, as shown in FIG. 1, a group of hooks per projection. In the shown example, a total of eight hooks are present, wherein four respective hooks are arranged along two parallel lines. The hooks thus form a total of four pairs, wherein the hooks of each pair face each other. Also arrangements in which the hooks are offset are possible, or a different number of hooks at each projection is possible. Furthermore, additional hooks can be provided in the area of the further portions of the first end 31. As schematically shown in FIG. 1 and as evident on the basis of the hooks 34a and 34c, the hooks are inclined outwardly and are directed towards the second end 35. As evident on the basis of the hooks 34b, these hooks can moreover be directed laterally outwardly, i.e. the free ends of the two hooks of each pair of hooks face away from each other. This design and this arrangement of the hooks at the outside of the metal frame 30 lead to an improved anchoring of the metal frame in the tissue of the left ventricular outflow tract of the heart.

In the present example, the second end 35 of the metal frame 30 has a circularly circumferential uniform edge. Further parts of the device for circulatory support of the heart are arranged inside this metal frame 30 or can be arranged therein after implantation of the holding means in a next step. These further parts are explained on the basis of the description of the following Figures.

FIG. 1 further schematically shows an electrical supply line 2, which is connected to the holding means in the area of the septum 13 and guided along the interventricular septum. The part of the supply line shown inside the left ventricle is referred to as intraventricular portion 2a or intracardiac portion 2a. As schematically shown in FIG. 1, the area of the apex of the left ventricle 22 comprises a through opening 21 through which the electrical supply line 2 is guided to the outside. The portion of the electrical supply line lying outside the heart is referred to as extracardiac portion 2b.

This extracardiac portion 2b of the electrical supply line can be guided directly to the outside of the skin surface of a patient or it can end inside the body and preferably has a plug-in coupling at its end, as will be described in the following. Alternatively, this electrical supply line can also be guided such that it is first guided through the muscular septum 13 into the right ventricle 12 and is guided via a through opening at the diaphragmal side or at the front wall of the right ventricle 24 to the outside, or it can be guided either through the interatrial septum or the ventricular septum to the right atrium and then transvenously via a large vein to the outside. The outer diameter and the design of the supply line are such that they seal the through opening 21 in the apex of the left ventricle 22 and, if applicable, the through opening in the muscular septum 13 and the through opening of the right ventricle 24 (see FIG. 5).

Figure 2:
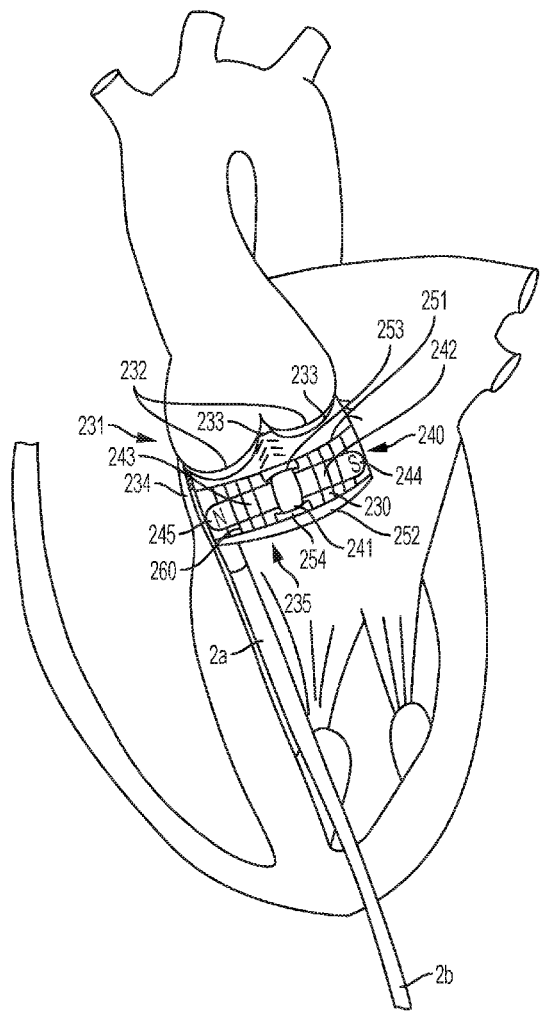
FIG. 2 shows a schematic view of a second embodiment of the invention, in which a self-expanding minimally invasively introducible stent graft or metal frame is arranged in the left ventricular outflow tract.

FIG. 2 shows a schematic view of a second embodiment of the device for circulatory support of the heart according to the invention, said device being arranged in the left ventricular outflow tract inside the left ventricle of the heart. In view of the anatomy and the arrangement of the holding means in the subcommissural triangle and the design of the holding means, reference is made to the above description relating to FIG. 1. In detail, FIG. 2 shows a holding means 230 in the form of a metal frame or metal structure. The metal frame 230 has a first end 231, which is designed in a manner comparable to that of the first end 31 of the metal frame 30 of FIG. 1. It comprises recesses 232, projections 233 and hooks 234. Reference is again made to the description of FIG. 1 relating to the design of the first end.

The metal frame further comprises a second end 235. Spaced from the first end, preferably adjoining the recesses 232, at least a first holding arm 251 is arranged, which extends diagonally and preferably perpendicularly to the axial direction from one side of the metal frame to the other. At least one second holding arm 252, which is arranged in the shown example parallel to the first holding arm 251, is arranged at the first end 235 or adjacent to the first end 235 of the metal frame 230. Alternatively, the second holding arm 252 can be arranged in a plane parallel to the plane in which the first holding arm extends, wherein the second holding arm is preferably arranged perpendicularly to the direction of the first holding arm. Instead of providing one holding arm, it is also possible to provide, e.g., two holding arms at the first end and at the second end, said respective holding arms forming, e.g., a cross. It is also possible to provide more than two holding arms, for example also an uneven number of holding arms. In the example shown in FIG. 2, only one holding arm 251 is provided at the first end, with a first bearing 253 being arranged thereon. A second bearing 254 is provided at the second holding arm 252. Both bearings are preferably in the middle of the metal frame 230 and lie opposite one another along a central axis of the metal frame 230. As schematically shown in FIG. 2, both bearings can have a respective concave bearing shell.

A rotor 240 is schematically shown inside the metal frame, said rotor having a rotational shaft 241 which is rotatably supported at one end in the first bearing 253 and at the other end in the second bearing 254. In the example schematically shown in FIG. 2, the rotor 240 has two opposite rotor blades 242, 243. When the rotor is driven, the blood present in the left ventricle 11 is pumped in the direction of the root of the aorta and flows through the aortic valve leaflet into the aorta. The rotor blades 242, 243 are realized in a suitable manner, in particular they comprise a corresponding inclination of the rotor blades, so that the blood flows in the desired direction when the rotor is rotated around the rotational shaft 241.

In the example of FIG. 2, the rotor is driven by means of an electric motor. In this shown example, the rotor comprises permanent magnets, wherein the first rotor blade 242 comprises a first permanent magnet 244, which is referred to as magnetic south pole, and the second rotor blade 243 comprises a second permanent magnet 245, which is referred to as magnetic north pole. The permanent magnets can be formed integrally with the rotor blades or as separate parts, for example, they can be provided in the form of coatings at the free ends of the rotor blades.

The electric motor further comprises a stator which is arranged inside the metal frame 230 and comprises electrical coils comprising wires. The coils can be present as separate parts or form an integral part of the metal frame 230. In FIG. 2, the coils are schematically indicated by the lines 260, which extend parallel to the axial direction from the first end to the second end of the metal frame.

Like in a conventional electric motor, a magnetic field can be generated by correspondingly activating the coils and supplying them with power, said magnetic field driving and rotating the rotor arranged inside. The rotational speed and the rotational power are adjusted by a suitable coil arrangement and suitable voltages. The power supply of the electric motor and the control of the rotational speed and the rotational power are controlled via the electrical supply line 2 by means of a control apparatus connected thereto. FIG. 2 only shows the intracardiac portion 2a of the electrical supply line and a part of the extracardiac portion 2b of the electrical supply line.

The second embodiment, which is schematically shown in FIG. 2, can be implanted by means of a catheter in the left ventricular outlet tract of the heart, as will be explained in more detail below. To this end, the metal frame 230 is collapsible and subsequently re-expandable, as already described in connection with FIG. 1, and also the common unit of stator and rotor is collapsible and can be brought in the operating position. Thus, the entire device can be implanted at the same time as a unit or it can be implanted in several subsequent steps, wherein first the holding means 230 is implanted, and, if the stator is a separate part, next the stator is implanted, and in a further step the rotor is implanted. Alternatively, the stator and the rotor can also be implanted together. In an alternative embodiment in which the stator is an integral component of the holding means, the rotor can be inserted after the holding means has been implanted.

Figure 3:
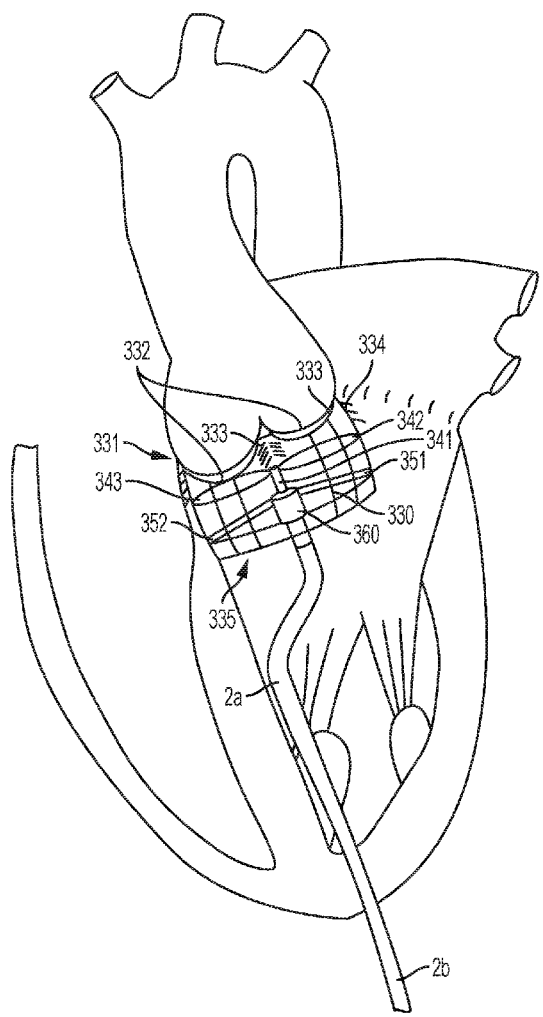
FIG. 3 shows a schematic view of a third embodiment of the invention, in which a self-expanding minimally invasively introducible stent graft/metal frame is arranged in the left ventricular outflow tract.

FIG. 3 shows a schematic view of a third embodiment of the device according to the invention. This device comprises a metal frame 330 which is comparable to the metal frame 30 of FIG. 1 and the metal frame 230 of FIG. 2. The metal frame has a first end 331 with a plurality of recesses 332 and projections 333 arranged therebetween. Hooks 334 are arranged at the projections 333. The metal frame further has a second end 335. The device is arranged in the left ventricular outflow tract of the heart in the same manner as described in connection with the devices of FIG. 1 and FIG. 2. Reference is made to the respective description.

Different from the embodiment of FIG. 2, in the example shown in FIG. 3, two holding arms 351, 352 are arranged at the second end of the metal frame, said holding arms being directed radially inwardly and having an electric motor 360 preferably releasably attached thereto. The electric motor 360 has a rotational shaft 341, wherein two opposing rotor blades 342 and 343 are arranged at the rotational shaft. At an end of the electric motor 360 that is opposite the rotational shaft, the electrical supply line is arranged. The electrical supply line 2, in the present case the intracardiac portion 2a, can be connected to the electric motor 360 by means of a plug or it can be firmly connected thereto. During operation of the electric motor, the rotor blades 342, 343 arranged at the rotational shaft are rotated such that the blood in the left ventricle is pumped in the direction of the root of the aorta through the aortic valve leaflets into the aorta.

In the third embodiment shown in FIG. 3, the electric motor is arranged in the area of the second end of the metal frame, and the rotational shaft as well as the rotor blades face in the direction of the first end 331 of the metal frame 330.

As will be explained in more detail below, the rotor blades are preferably collapsible and can be implanted together with the electric motor by means of a catheter. For this purpose, either the metal frame 330 is first implanted and then the motor with the rotor blades arranged thereon, or both parts are implanted together as a unit. The electric motor is preferably closed and completely sealed. As schematically shown, it has a cylindrical shape in which the units such as stator and rotor are integrated. The motor can have different configurations which are known in connection with electric motors. It can be configured as a brushless DC motor with electronic converter, as an EC motor or as a permanently excited synchronous motor or as an AC motor. The holding arms 351, 352 are preferably realized as metal supports. The latter can be made in one piece with the metal frame. This accordingly also applies to the structure of the first and second holding arms of the device of FIG. 2.

The rotational speed and rotational power can be adjusted on the basis of the voltage and the respective design of the electric motor. The pumping power can be adjusted in accordance with the rotational power of the electric motor and the design of the rotor blades.

Figure 4:
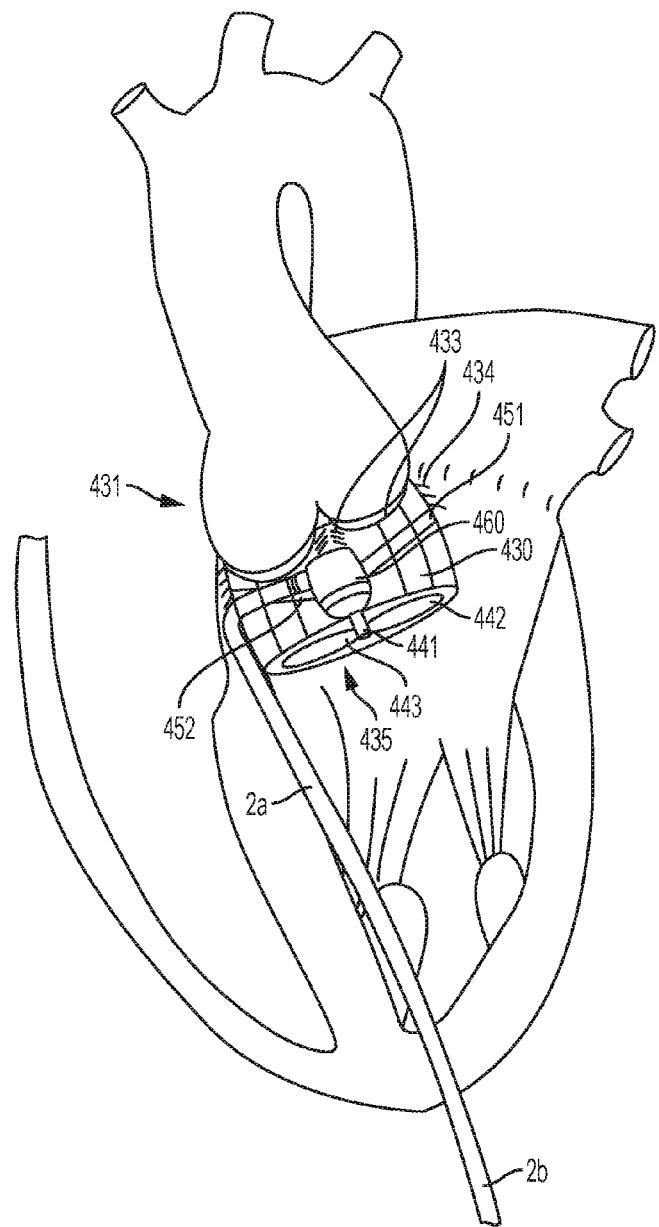
FIG. 4 shows a schematic view of a fourth embodiment of the invention, in which a self-expanding minimally invasively introducible stent graft/metal frame is arranged in the left ventricular outflow tract.

FIG. 4 shows a schematic view of a fourth embodiment of the device according to the invention. This embodiment is comparable to the third embodiment of FIG. 3. Therefore, in the following only the differences will be discussed. As to the rest, reference is made to the description of FIG. 3, FIG. 2 and FIG. 1. When comparing FIGS. 3 and 4, it is evident that the insertion direction of the electric motor 460 inside the metal frame 340 is different. The metal frame 430 is arranged in the same manner as described in connection with the holding means of FIGS. 1, 2 and 3 in the left ventricular outflow tract of the heart. In particular, hooks 434 are provided at the projections 433 at the first end 431 of the metal frame. In the embodiment shown in FIG. 4, two holding arms 451, 452 are schematically arranged in a manner opposing each other in the area of the first end of the metal frame. These holding arms are directed radially inwardly and, as schematically shown, they are arranged at an angle with respect to a plane in the direction towards the second end 435 of the metal frame 430. The electric motor 460 is attached, or releasably attached, to the ends of the holding arms 451, 452.

The electric motor 460 has a rotational shaft 441 at which two opposing rotor blades 442, 443 are arranged. The rotor blades are in the plane adjacent to the second end 435 of the metal frame 430 or directly in the plane in which the second end 435 lies. In the embodiment shown in FIG. 4, the electrical supply line 2 is connected at the side of the electric motor 460, exemplarily at the first end of the electric motor 460. Here, the electrical supply line is guided through an opening in the metal frame or around the metal frame 430 to the outside of the metal frame in the area of the muscular septum 13 and further in the direction of the apex of the left ventricle. The intracardiac portion 2a and a part of the extracardiac portion 2b of the electrical supply line are shown here. With respect to the further description of the electric motor as well as the further structure of the device, reference is made to the description of FIG. 3.

Figure 5:
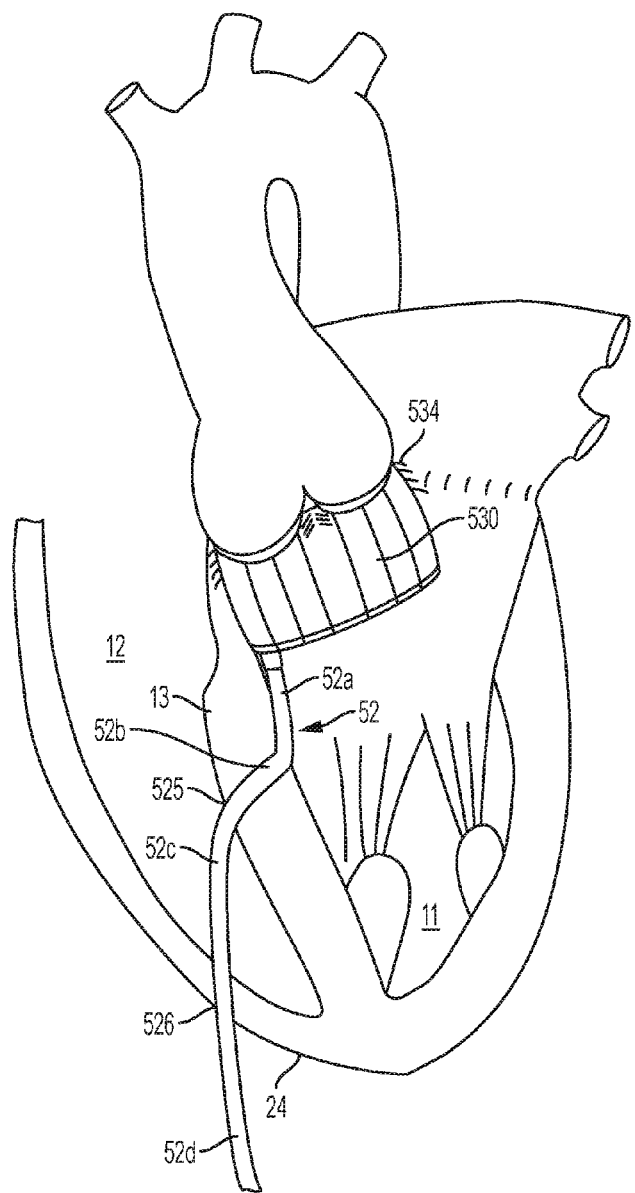
FIG. 5 shows a schematic view of a fifth embodiment of the invention, in which a self-expanding minimally invasively introducible stent graft/metal frame is arranged in the left ventricular outflow tract.

FIG. 5 shows a fifth embodiment of the invention, in which the metal frame 530 is shown in the left ventricular outflow tract of the heart. The metal frame 530 comprises the same parts as the metal frames described in connection with FIG. 1, 2, 3 or 4. The hooks 534 are exemplarily shown here. As in particular comparable with the first embodiment of FIG. 1, an electrical supply line 52 is arranged at the second end of the metal frame 530. Like in FIG. 1, the device is arranged in the area of the muscular septum 13. In contrast to the embodiment of FIG. 1, the supply line 52a does not lead directly to the apex of the left ventricle but through a through opening 525 in the muscular septum 13 further into the right ventricle 12 and through a through opening 526 in the wall of the right ventricle in the vicinity of the apex 24 of the heart. The electrical supply line thus has a left ventricular portion 52a or intracardiac portion 52a, a transseptal portion 52b leading through the through opening 525 in the muscular septum 13, a right ventricular portion 52c and an extracardiac portion 52d, of which only a part is visible.

This embodiment of the invention is advantageous in that a sealing of the through opening 526 in the apex 24 of the right ventricle can be achieved safely by means of the electrical supply line extending through it. The pressure in the right ventricle is generally lower than the pressure in the left ventricle. This leads to a more easily achievable sealing at the through opening 526.

In the fifth embodiment shown in FIG. 5, the pump arrangements shown in FIG. 2, FIG. 3 and FIG. 4 can be used. Therefore, reference is made to the respective descriptions. In view of the holding means, reference is moreover made to the description relating to FIG. 1.

Figure 6:
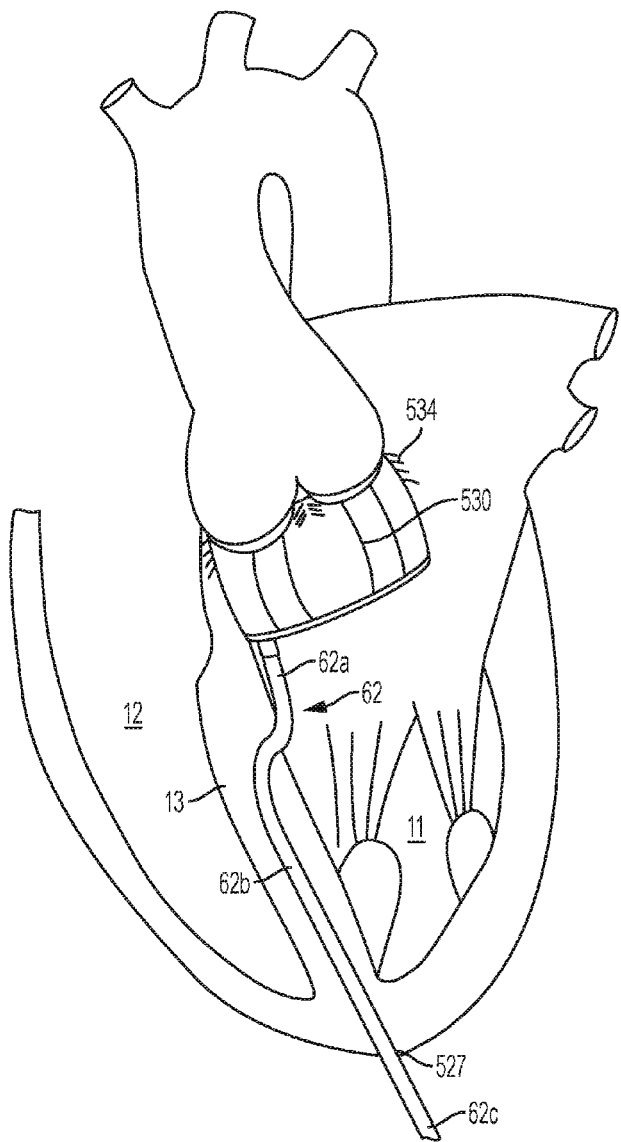
FIG. 6 shows a schematic view of a sixth embodiment of the invention, in which a self-expanding minimally invasively introducible stent graft/metal frame is arranged in the left ventricular outflow tract.

FIG. 6 shows a schematic view of a sixth embodiment of the device according to the invention. This embodiment largely corresponds to the fifth embodiment, so that reference is made to the above description of FIG. 5 in connection with FIGS. 1 to 4. The device comprises a metal frame 530, which is comparable to the metal frame 530 and the corresponding metal frames of FIGS. 1 to 4, wherein, for example, the hooks 534 are shown. In contrast to the embodiment of FIG. 5, the electrical supply line 62 is divided into a left ventricular portion 62a, a septal portion 62b and an extracardiac portion 62c. The electrical supply line 62 is connected to the second end of the metal frame 530 and leads directly adjacent to the first end of the metal frame into the muscular septum 13. The supply line is further guided through the muscular septum 13 and exits at the apex. In other words, there is provided a through opening 527 which extends through the muscular septum 13 in the longitudinal direction from the side of the left ventricle 11 to the outside of the heart.

The relatively long way of the electrical supply line through the elongate through opening 527 in the muscular septum 13 leads to an improved sealing against the pressure prevailing in the left ventricle 11.

The pump arrangements shown in FIG. 2, FIG. 3 and FIG. 4 can be used in the sixth embodiment shown in FIG. 6. Therefore, reference is made to the respective description. In view of the holding means, reference is moreover made to the description in connection with FIG. 1.

Figure 7:
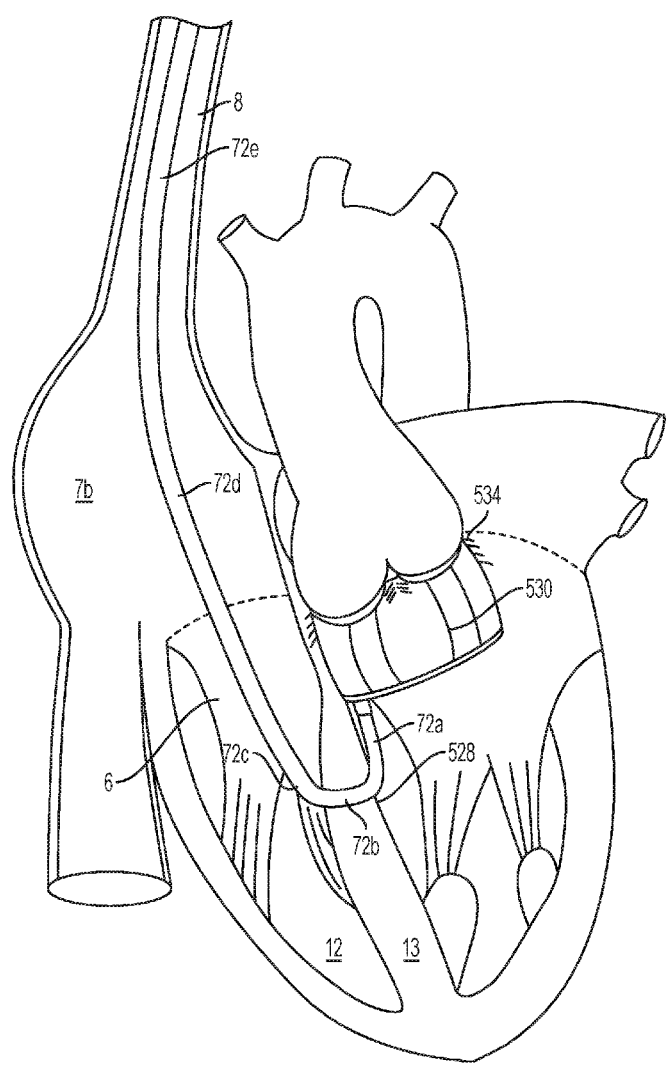
FIG. 7 shows a schematic view of a seventh embodiment of the invention, in which a self-expanding minimally invasively introducible stent graft/metal frame is arranged in the left ventricular outflow tract.

FIG. 7 shows a seventh embodiment of the invention, wherein the metal frame 530 is shown in the left ventricular outflow tract of the heart. The metal frame 530 comprises the same parts as the metal frames described in connection with FIGS. 1 to 5. The hooks 534 are exemplarily shown. As in particular comparable with the first embodiment of FIG. 1, an electrical supply line 2 is arranged at the second end of the metal frame 530. Like in FIG. 1, the device is arranged in the area of the muscular septum 13. In contrast to the embodiment of FIG. 1, the supply line 2a does not lead directly to the apex of the left ventricle but through a through opening 528 in the muscular septum 13 further into the right ventricle 12 and from there through the tricuspid valve 6 into the right atrium 7b, and it is then guided through a vena cava 8 to a large peripheral vein and from there through a through opening into the subcutaneous tissue (not shown). The electrical supply line thus has a left ventricular portion 72a, a transseptal portion 72b extending through the through opening 528 in the muscular septum 13, a right ventricular portion 72c and a right atrial portion 72d and a caval portion 72e, of which only a part is visible.

This embodiment of the invention is advantageous in that a sealing of the through opening in a large vein (e.g. subclavian vein, jugular vein, axillary vein, or femoral vein) can be achieved safely by means of the electrical supply line extending through it. A through opening of this kind is nowadays often used for implanting cardiac pacemakers, which generally does not lead to any problems. The venous pressure is generally much lower than the pressure in the heart. This leads to a more easily achievable sealing at the through opening from the vein into the subcutaneous tissue.

Figure 8:
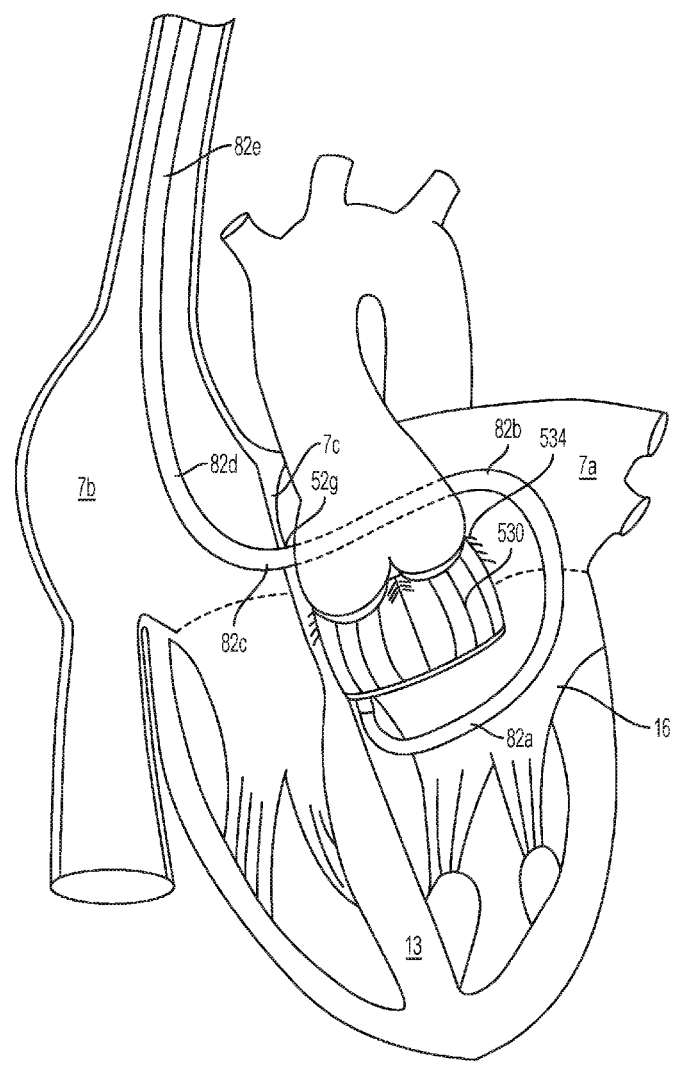
FIG. 8 shows a schematic view of an eighth embodiment of the invention, in which a self-expanding minimally invasively introducible stent graft/metal frame is arranged in the left ventricular outflow tract.

FIG. 8 shows an eight embodiment of the invention, in which the metal frame 530 is shown in the left ventricular outflow tract of the heart. The metal frame 530 comprises the same parts as the metal frames described in connection with FIG. 1, 2, 3 or 4. The hooks 534 are exemplarily shown here. As in particular comparable with the first embodiment of FIG. 1, an electrical supply line is arranged at the second end of the metal frame 530. Like in FIG. 1, the device is arranged in the area of the muscular septum 13. In contrast to the embodiment of FIG. 1, the supply line does not directly lead to the apex of the left ventricle but through the mitral valve 16 into the left atrium 7a, then further through the interatrial septum 7c into the right atrium 7b, and it is then guided through a vena cava 8 to a large peripheral vein and from there through a through opening into the subcutaneous tissue (not shown). The electrical supply line thus has a left ventricular portion 82a, a left atrial portion 82b, a transseptal portion 82c leading through the through opening 529 in the interatrial septum 7c, a right atrial portion 82d and a caval portion 82e, of which only a part is visible.

The access through the atrial septum is nowadays often used percutaneously for diagnosing and treating cardiac arrhythmia in a catheter laboratory. This embodiment of the invention is advantageous in that a sealing of the through opening in a large vein can be safely achieved by means of the electrical supply line extending through it. A through opening of this kind is nowadays often used for implanting cardiac pacemakers, which, as a rule, does not lead to any problems. The venous pressure is generally much lower than the pressure in the heart. This leads to a more easily achievable sealing at the through opening from the vein into the subcutaneous tissue.

Figure 9:
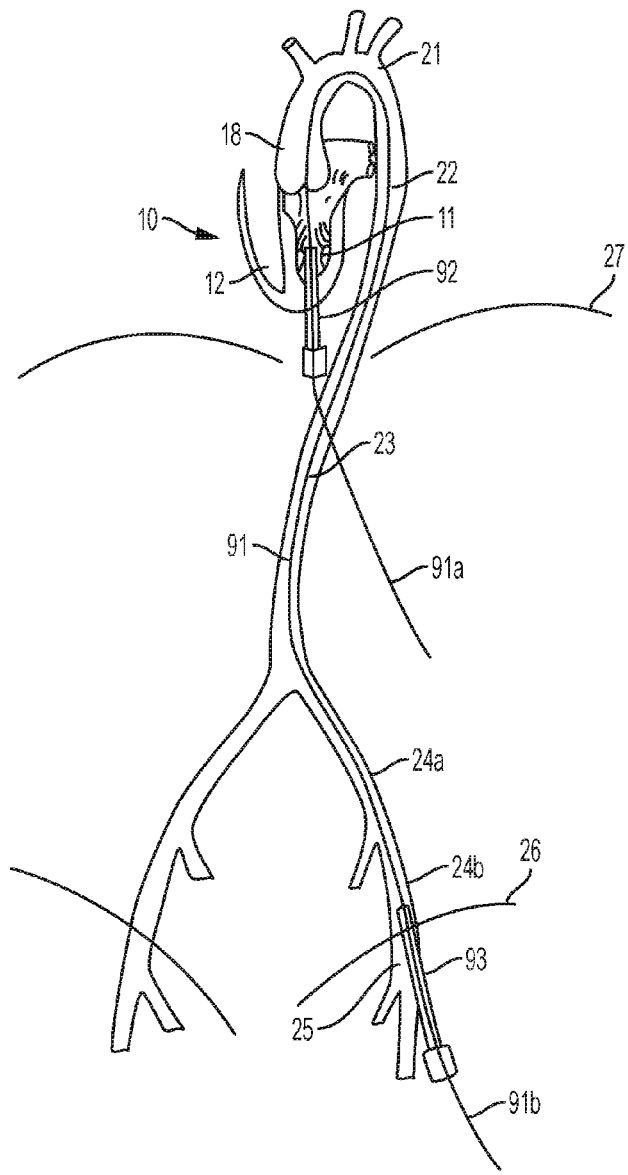
FIG. 9 shows a schematic view of a first embodiment of a system according to the invention for handling the device according to the invention.

FIG. 9 schematically shows a first embodiment of a system according to the invention for handling the device of FIGS. 1 to 6 of the invention. First of all, the anatomy is explained. FIG. 9 schematically shows a part of the heart 10, namely the left ventricle 11 and the right ventricle 12. Said part of the heart is followed by the aorta, and the ascending aorta 18, the aortic arch 21, the descending aorta 22 and the thoracoabdominal aorta 23 are following. The latter is further connected to the common iliac artery 24a and the external iliac artery 24b and further with the common femoral artery 25 in the groin 26. The diaphragm 27 is also schematically shown.

The embodiment of a system for handling the device for circulatory support of the heart according to the invention as shown in FIG. 9 serves for an endovascular implantation of the device. The embodiment for handling the device according to the invention comprises an endovascular wire 91 having two ends 91a and 91b and being inserted through a puncture site in the heart or in a large vein into the vessel system. In the area of the apex of the heart 10, an arterial lock 92 is inserted into the left ventricle, either via the apex of the heart or via a right ventricular transseptal access, a septal access, by directly puncturing the heart, or by puncturing a large vein and subsequently puncturing the atrial septum or the ventricular septum. One end 91b of the wire is guided outwardly via the aorta 18, 21, 22, 23 and the iliac artery 24 to the femoral artery 25. It is thus possible to pull simultaneously at both ends of the wire ("tooth-floss method"), wherein a precise control of the guide wire and thus the heart support system is possible during insertion and releasing.

FIG. 9 further shows an arterial sheath 93 in the femoral artery.

Once the wire has been inserted, the device is inserted into the vessel system through the femoral access in the area of the groin and moved via the endovascular wire to the heart and is then released in the left ventricular outflow tract of the heart and anchored in the subcommissural triangles. It will be shown below in connection with FIG. 17 that a precise repositioning of the anchoring means can be achieved by pulling at both ends of the guide wires, leading to a decrease in the diameter.

The electrical supply line connected to the device is pulled out by means of an endovascular wire through the puncture site in the heart after the device has been anchored in the left ventricular outflow tract. After releasing the device, the endovascular wire serves for pulling the electrical supply line out of the left ventricle of the heart, and the supply line is pulled out through the access way (possibly left ventricle, septum, right ventricle, large vein after transseptal or transatrioseptal puncturing). The electrical supply line has a larger diameter than the wire, so that the through opening in the heart is sealed by means of the electrical supply line.

The endovascular wire is finally pulled completely out of the body and thereby pulls the electrical supply line also to the intended site at the surface of the body of the patient. As already mentioned, the electrical supply line can have an electrical coupling at its free end, wherein said electrical coupling can either be connected directly to an apparatus for supplying voltage and for controlling the device or it can be connected to a plug-in connection from which the electrical supply line is guided further outwardly to an apparatus for supplying voltage and for controlling the device.

FIGS. 10a to 10e show various views of details of a ninth embodiment of a device according to the invention. This ninth embodiment can be implanted in the left ventricular outflow tract inside the left ventricle of a heart, as described, e.g., on the basis of FIG. 1. FIG. 10a shows a side view of the device according to the invention, which comprises a holding means in the form of a metal frame 730. In particular from the top views of FIGS 10b and 10c it is evident that the metal frame 730 has a cylindrical shape. As suggested in FIG. 10a, the cylindrical shape can have a barrel shape in which the outer surface is bulged outwardly. The holding means further comprises a first end 731, which forms an anatomically shaped subvalvular part of the metal frame which is anchored in the subcommissural triangles in the left ventricular outflow tract. As already described above in connection with FIGS. 1 to 6, three recesses 732 being adapted to the anatomic shape are formed at the first end 731. Respective projections 733 having one hook or a plurality of hooks 734 at their outer sides are present between the recesses.

FIG. 10*a* schematically shows a first holding arm 751, which extends perpendicularly relative to the image plane. This first holding arm 751 is fixed to the metal frame 730 in the area of the first end 731. FIG. 10*a* further schematically shows a second holding arm 752 at the second end 735 of the metal frame 730. This holding arm 752 extends in the plane of the drawing, i.e. substantially perpendicularly with respect to the first holding arm 751. In particular from the detailed view of FIG. 10*d* it is evident that the first holding arm 751 has a first bearing 753 which is cup shaped, i.e. has a concave bearing shell. The second holding arm 752 has a second bearing 754 which, in the present example, is knob-shaped, i.e. has a bearing projection. It is also schematically shown in FIG. 10*d* that the rotor 740 has a rotational shaft 741 which is convex at the first end and concave at the second end, wherein the design, in particular the shape and size, is adapted to the corresponding bearing shell 753 and/or the bearing knob 754. Two opposing rotor blades 742, 743 are arranged at the rotational shaft 741. As evident from the schematic top view of FIG. 10*b*, the rotor blades each have an asymmetric shape. The rotor blade 742 is essentially triangular with a convex front side 742*a*, a concave rear side 742*b* and a circular free end 742*c*. The second rotor blade 743 is arranged approximately 180° offset thereto, said second rotor blade also having a convex front side 743*a*, a concave rear side 743*b* and a circular free end 743*c*. With reference to FIG. 10*d* it is pointed out that the rotor blades can have a selectable angle of attack in the axial direction, so that the pumping power is adjusted accordingly when the rotor is rotating.

In the top view of FIG. 10*c* the rotor has been omitted. The first holding arm 751 at the first end and the second holding arm 752 at the second end of the metal frame 730 are shown. As evident from a combination of FIGS. 10*a* and 10*c*, the electrical supply line 2 is arranged or connected in the area of the second end 735 adjacent to an end of the second holding arm 752.

FIG. 10*e* schematically shows the stator with a plurality of electrical coils, wherein in this example the coils are arranged in pairs opposite to one another. In the clockwise direction, electrical coils 761 and 762 are shown in a manner opposite to one another. The next pair is offset by 90° relative to the rotational direction and is formed by coils 763 and 764. Between this first and second pairs of coils, coils 765 and 766 are shown in a manner opposite to one another and form a third pair of coils. Starting from this third pair of coils, coils 767 and 768 are arranged in a manner offset by 90° and opposite to one another and form a fourth pair of coils. In the middle of the stator 760, the rotational shaft 741 is schematically shown.

As comparable with the embodiment described on the basis of FIG. 2, the ninth embodiment comprises rotor blades having permanent magnets 744 and 745 formed at their respective ends. By accordingly activating the pairs of coils and correspondingly supplying them with power, a magnetic field is generated, which drives and accordingly rotates the rotor. In the present example, each of the four pairs of coils has an opposite winding direction, so that in case current flows through an individual pair of coils, opposite electromagnetic fields are generated. An own current is flowing through each pair of coils, wherein said current flow is temporally offset relative to the next pair of coils and possibly has a sine wave and leads to a rotational acceleration of the rotor with its blades in the desired direction. In case of a temporally offset current flow through the stator coils, magnetically opposite magnetic poles north and south are generated, which move in a circle with the frequency of the temporally offset sine-shaped current flows. These magnetic poles attract the corresponding opposite magnetic poles generated by the permanent magnets at the rotor blades, so that the rotor is rotated. By accordingly switching the magnetic field further, the rotor can be rotated.

The motor can have different electric motor designs. The motor can be, e.g., a brushless DC motor with electronic converter, i.e. a so-called BLDC motor, also known as electronically commutating DC motor. In BLDC motors, the rotor is normally realized by means of a permanent magnet, the stationary stator comprises the coils, which are activated in a temporally offset manner by an electronic circuit, so that a rotational field is generated, causing a rotational moment at the permanently excited rotor. Preferably it is a stepper motor, i.e. the commutation of the BLDC motor is realized independent of the position, rotational speed and moment loading of the rotor. By means of the magnetic field of the stator, the permanently magnetic rotor of the stepped motor is aligned such that a rotational movement is generated. The motor can also be realized as a permanently excited synchronous motor or as an AC motor.

FIGS. 11*a*, 11*b* and 11*c* show schematic views of a first embodiment of a rotor with foldable rotor blades. This rotor can be used, e.g., in the second embodiment of FIG. 2 or in the ninth embodiment of FIG. 10, wherein the rotor is inserted by means of a catheter 910 after the metal frame with the stator therein has been anchored in the left ventricular outflow tract. The rotor 940 has a rotor shaft 941 at which rotor blades 942, 943 are arranged in such a manner that the rotor blades are foldable. FIG. 11*a* schematically shows the rotor with foldable rotor blades inside a tubular flexible insertion instrument of a catheter. The rotor blades 942 and 943 are folded substantially along the rotational shaft 941. FIG. 11*b* shows the rotor blades in the semi-unfolded state, after they have been released from the catheter. FIG. 11*c* shows the rotor with completely unfolded rotor blades. In this first embodiment of the rotor, the rotor blades are folded diametrically, i.e. the first rotor blade 942 faces towards a first end of the rotational shaft 941 and the second rotor blade 943 faces towards a second end of the rotational shaft 941.

FIGS. 12*a*, 12*b* and 12*c* schematically show a second embodiment of a rotor with foldable rotor blades. The rotor 1040 has a rotational shaft 1041 at which two rotor blades 1042, 1043 are arranged opposite one another. In FIG. 12*a* the rotor is schematically shown with folded blades, wherein both rotor blades are folded with their free ends in the same direction and end at an end of the rotational shaft 1041 of the rotor 1040. Inside the catheter 1010 or the flexible insertion instrument, the rotor blades are completely folded. FIG. 12*b* shows the rotor with semi-unfolded rotor blades. In FIG. 12*c* the rotor blades are completely unfolded.

In both embodiments of FIGS. 11 and 12, the rotor blades are arranged at the rotational shaft of the rotor preferably by means of a hinge or joint. Alternatively, the rotor blades can be collapsible and unfoldable. Thus, the rotor blades can be folded and unfolded again. Preferably, unfolding of the rotor blades occurs automatically as a consequence of a restoring force caused in the hinge or joint and/or in the rotor blades. Alternatively, the rotor blades can be unfolded by means of the catheter instrument.

Figure 13A:
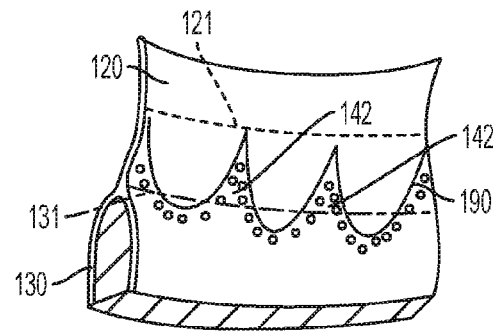
FIG. 13*a* shows a schematic developed view for anatomically describing the left ventricular outflow tract and the site where the device according to the invention is arranged.
Figure 13B:
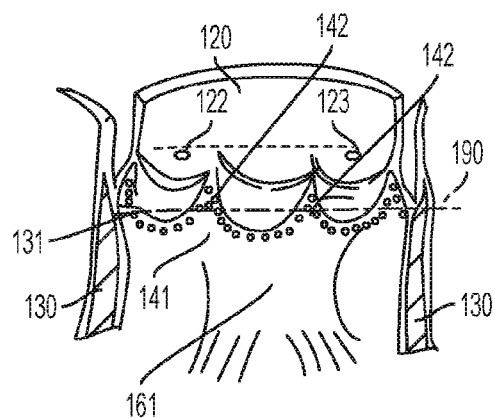
FIG. 13*b* shows a schematic developed view for anatomically describing the left ventricular outflow tract and for explaining the site where the device according to the invention is arranged.

FIGS. 13a and 13b show schematic developed views for anatomically describing the left ventricular outflow tract and the site where the device according to the invention is arranged. The device according to the invention has been omitted and the dotted line shows the anatomic site where the metal frame or stent graft is anchored. For example, the device can be implanted by means of the system for handling the device described with reference to FIG. 9. FIG. 13a schematically shows the anatomy with the aorta ascendens 120, the sinotubular junction 121 and the aortic valve annulus 190. Furthermore, the ventriculo-arterial junction 131 and the ventricular myocardium 130 are schematically shown. In this area, the subcommissural triangles 142 are schematically shown. Thus, the arterial wall on the ventricular side of the aortic valve is shown. (Synonyms of the anatomical structures in German: subkommisurales Dreieck=subcommissural triangle, ventrikularer Anteil der Aortenwand=ventricular portion of the aortic wall.)

FIG. 13b shows further details of the anatomy, wherein in the area of the aorta ascendens 120, the right coronary ostium 122 and the left coronary ostium 123 are shown. Furthermore, the membranous part of the interventricular septum 141 is schematically shown below the subcommissural triangles. Directed further below from there, the mitral valve is schematically shown, i.e. the front leaflet of the mitral valve 161. As already discussed, the dotted lines in FIGS. 13a and 13b are the sites where the device according to the invention is anchored.

Figure 13C:
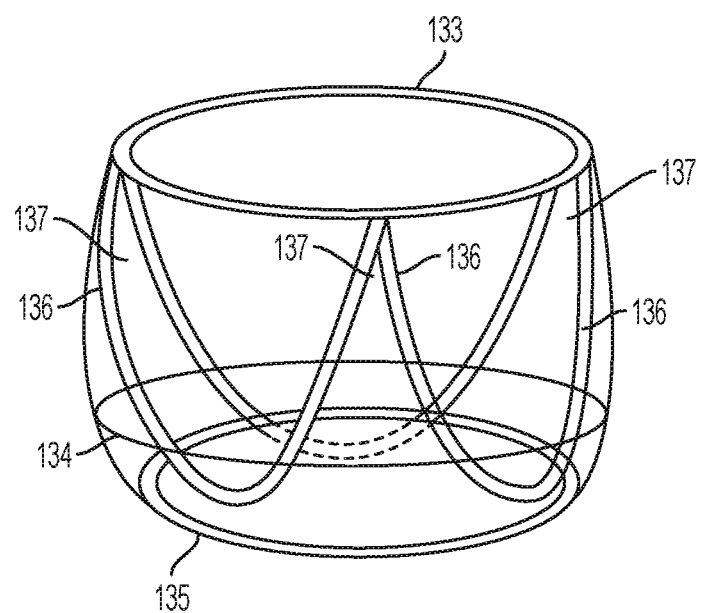
FIG. 13*c* shows a schematic view of the aortic root anatomy for explaining in more detail the position of the sub-commissural triangles.

FIG. 13c shows a schematic view of the aortic root anatomy. More specifically FIG. 13c shows the sinotubular junction 133, the aortoventricular junction 134 and the basal ring 135. The attachment edges 136 of the aortic valve leaflets are shown as semicircular curves extending from the sinotubular junction 133 in the direction of the basal ring 135. The subcommissural triangles 137 are the part of the fibrous aortic wall on the ventricular side of the aortic valve above the basal ring 135 and above the aortoventricular junction 134.

Anchoring of the holding means is performed in the fibrous tissue above the basal ring 135 and above the aortoventricular junction 134 but below the aortic valve leaflets. Preferably, the holding means is anchored in the three small triangular zones between two neighboring attachment edges 136 of the aortic valve leaflets.

Figure 14:
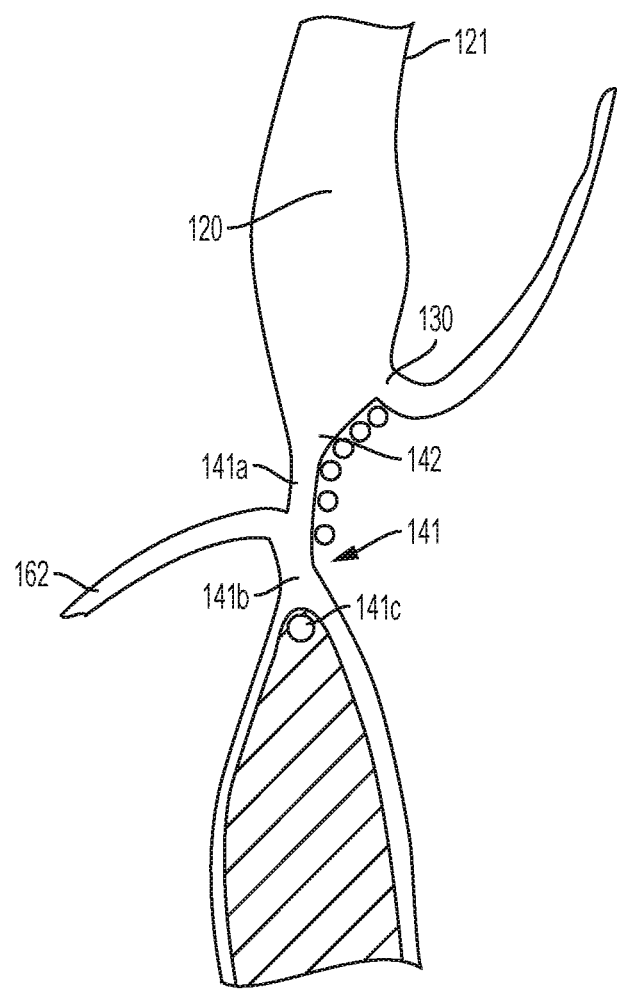
FIG. 14 shows a schematic view of a cross-section through the membranous septum for anatomically describing the front part of the left ventricular outflow tract and for explaining the site where the device according to the invention is arranged.

FIG. 14 shows a schematic view of a cross-section through the membranous septum for anatomically describing the front part of the left ventricular outflow tract and for explaining the site where the device according to the invention is arranged. The dotted line again shows the anatomic site where the metal frame/stent graft is anchored. Equal parts, which are visible in FIG. 13, are marked here with the same reference numbers. Thus, reference is made to the above description of FIG. 13. In particular the portion of the \ membranous interventricular septum 141 having an atrial portion 141a and a ventricular portion 141b is schematically shown. This cross-section additionally schematically shows the bundle of His 141c, which guarantees the atrioventricular conduction of the heart. It is schematically shown that the tricuspid valve leaflet 162 is arranged at the interventricular septum on the right side of the heart, which is opposite the side at which the device according to the invention is anchored.

Figure 15A:
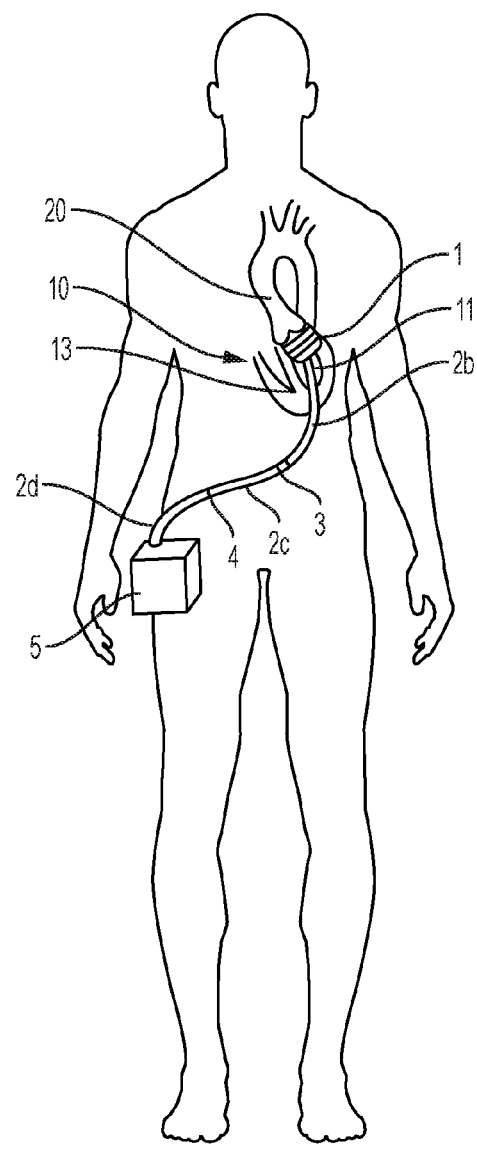
FIG. 15a shows a schematic view of a further embodiment, wherein the parts lying inside the body of a patient are visible.

FIG. 15a is a schematic view of the device for circulatory support of the heart according to the invention, which is implanted in the left ventricle, as well as of the supply lines connected thereto and the control apparatus lying outside the body of a patient. In the shown example, the device 1 for circulatory support of the heart is implanted in the heart 10. The electrical supply line is guided through the apex of the left ventricle towards the outside of the heart. The extracardiac portion of the electrical supply line 2b is schematically shown. The extracardiac portion of the control line 2b ends at an electrical connector 3. This connector 3 is preferably arranged in the subcutaneous tissue of the abdomen. The connector serves for connecting a second electrical supply line 2c and 2d, which leads to a control apparatus 5. If the portion of the supply line lying outside the body is damaged or in case of an infection or in case the supply line does not correctly heal into the skin outlet site 4, this portion of the supply line can be replaced and separated from the implanted portion of the supply line by means of the connector, and a new portion of the supply line can be connected to the implanted part or the new portion of the supply line can be arranged at another skin outlet site. This is advantageous because it is not necessary to explant and replace the entire system and an infection of the entire system can be avoided. The control apparatus 5 lies outside the body of the patient. The control apparatus 5 serves for providing the supply voltage for the electrical device as well as for supplying the corresponding control signals. Furthermore, sensor signals can be transmitted via the electrical supply line from the electrical device to the control apparatus 5. The control apparatus is preferably battery-driven, wherein the contained batteries are either chargeable or replaceable. The second electronic supply line can be divided into a first portion 2c, which is guided in the subcutaneous tissue, and a second portion 2d, i.e. the extracorporal portion of the electrical supply line. The electrical supply line exits the body at an exit site 4 which, in the present case, lies approximately in the area of the right front abdomen.

Figure 15B:
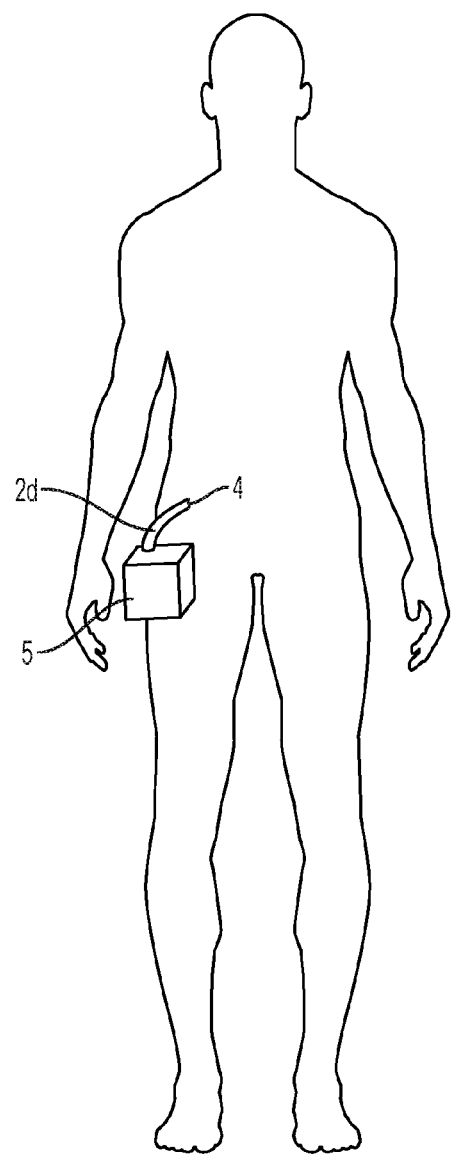
FIG. 15b shows a schematic view of a further embodiment, wherein the parts lying inside the body of a patient are not visible.

FIG. 15b is a schematic view of the same embodiment as that of FIG. 15a, wherein the parts lying in the body of the patient are not visible.

Figure 16A:
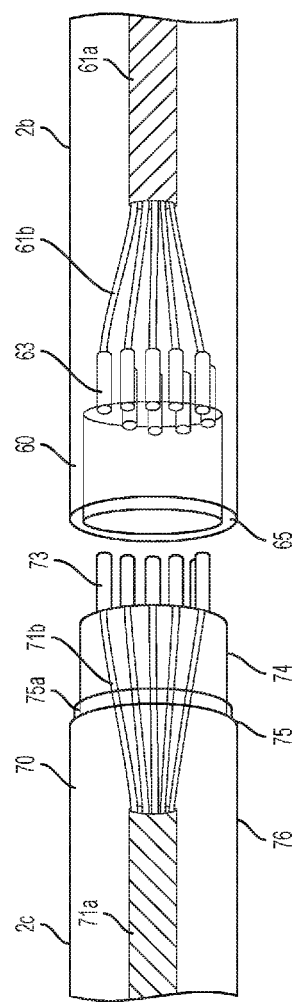
FIG. 16a shows an enlarged schematic view of a first embodiment of a plug-in connector for a supply line of the device according to the invention, wherein the plug and the coupling are disconnected from each other.
Figure 16B:
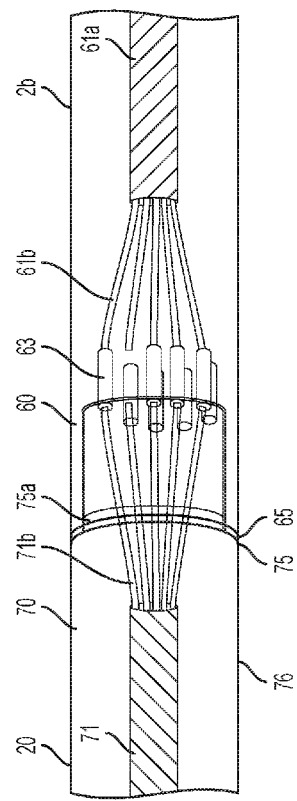
FIG. 16b shows an enlarged schematic view of a first embodiment of a plug-in connector for a supply line of the device according to the invention, wherein the plug is connected to the coupling.

FIG. 16a is an enlarged schematic view of a first embodiment of a connector 3, which is schematically shown in FIG. 15a, wherein this connector is realized as a plug-in connector. In FIG. 16a, the plug-in connector is schematically shown, wherein the plug and the coupling are separate from each other. In FIG. 16b, the plug is connected to the coupling. In the shown example, the plug-in connector has a coupling 60 and a plug 70. The coupling 60 is arranged at the end of the extracardiac portion 2b of the electrical supply line. The plug 70 is arranged at the end of the intracorporal portion 2c of the electrical supply line. A cable 61a with a plurality of leads 61b is arranged inside the electrical supply line. Each individual lead 61b is connected to a corresponding connection sleeve 63 of the coupling 60. In the shown example, a total of nine connection sleeves are arranged on a circle in the coupling. The connection sleeves end at a distance from the end of the coupling 60. On the other side, the plug 70 is shown. A cable 7a with a plurality of leads 71b is arranged inside the supply line 2c. Each lead is electrically connected to a corresponding pin 73 of the plug. The pins project from the end of the plug 70. The length of the pins is adapted to the length of the connection sleeves. In a first portion 74, the plug has a reduced diameter. In front of a stepped projection 75 on a second portion 76 with larger diameter, the plug has a sealing ring 75a. As schematically shown in FIG. 16b, the plug is inserted into the provided cylindrical recess in the coupling so far that, on the one hand, the pins 73 are inserted into the corresponding connection sleeves 63 and, on the other hand, a face 65 of the coupling 60 adjoins the stepped projection 75 of the plug. As schematically shown, the sealing ring 75a is inside the recess in the coupling 60. Thus, a water-proof and reliable electrical connection between the two ends of the electrical supply line is achieved.

Figure 17A:
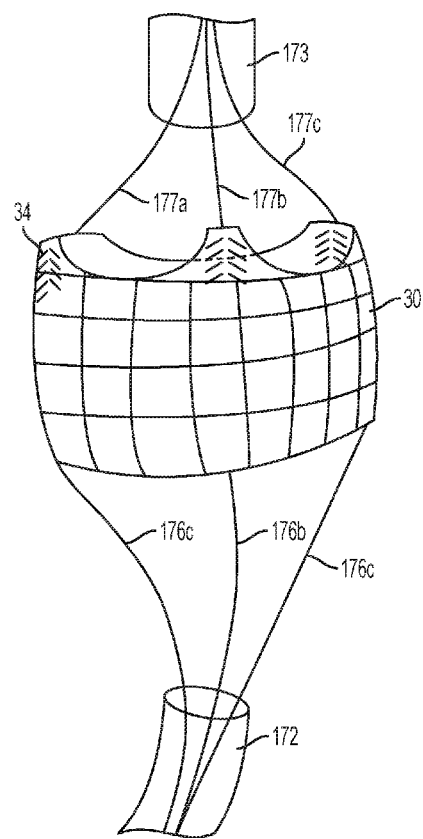
FIG. 17a shows an enlarged schematic view of a further embodiment for handling and in particular for repositioning the device according to the invention, wherein the stent graft/metal frame has a first, relatively large diameter.
Figure 17B:
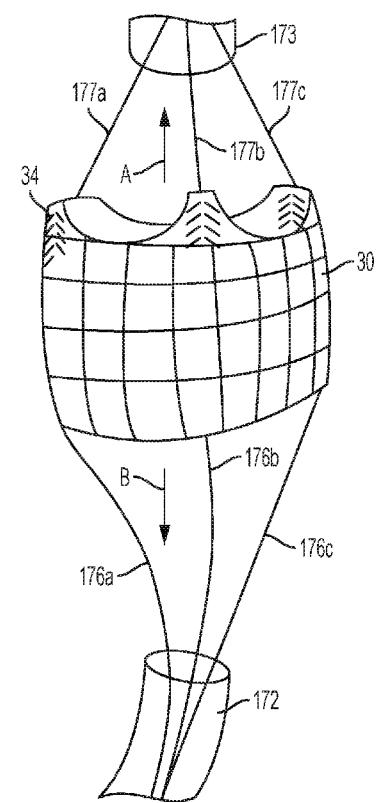
FIG. 17b shows an enlarged schematic view of a further embodiment for handling and in particular for repositioning the device according to the invention, wherein the stent graft/metal frame has a second, relatively small diameter.

FIGS. 17a and 17b show an enlarged schematic view of a further embodiment for handling and in particular for repositioning/adjusting the device according to the invention. As schematically shown in FIG. 17a, a metal frame 30 has a first relatively large diameter. For handling and for repositioning the metal frame, the metal frame is brought to a smaller diameter. For example, the metal frame can be reduced to the diameter shown in FIG. 17b. In this example, the diameter is reduced by applying a tension force to both ends of the metal frame. In this example, three wires 177a, b and c catch hold of the first end of the metal frame, wherein these wires can be attached to the projections in the area of the first end. These wires are guided in the aorta ascendens via a first catheter 173 and via a long lock to the arteria femoralis, so that it is possible to pull said wires from outside. In this example, also three wires 176a, b and c can be attached to the second end of the metal frame 30, said wires being guided via a second catheter 172 through an arterial lock (not shown) in the apex of the heart, in the right ventricle or in a large vein to the outside of the body. If, on the one hand, the wires 177a, b, c are pulled in the direction of the arrow A and, on the other hand, the wires 176a, b, c are pulled in the direction of the arrow B, the shape of the metal frame can be changed such that a smaller diameter is present and thus at the same time the anchoring of the device in the left ventricular outflow tract is released. In this manner, the metal frame is brought to a partially collapsed state. If the metal frame or stent graft is self-expandable, the metal frame returns into the fully expanded state when the tensile forces are decreasing.

The ends of the endovascular wires 176a, b, c are realized as eyes or wire loops and can be attached to accordingly shaped hooks (not shown) in the area of the second end of the metal frame. Likewise, the endovascular wires 177a, b, c can have eyes or can be realized as wire loops, which can be connected to corresponding hooks (not shown) at the first end of the metal frame. After repositioning or after handling of the device, the wires can be released from the first and/or second end and pulled out to the outside.

This device is advantageous in that an implanted device can be newly positioned, because the landing zone for the anchorage is relatively narrowly defined in terms of anatomy (see FIGS. 13 and 14), or, if necessary, can be removed completely from the heart.

In the above embodiments the device for supporting the heart has been described with reference to an implantation in the left ventricular outflow tract. However, it is explicitly pointed out that the device can also be arranged in the right ventricular outflow tract, so that the description similarly applies.

Figure 18:
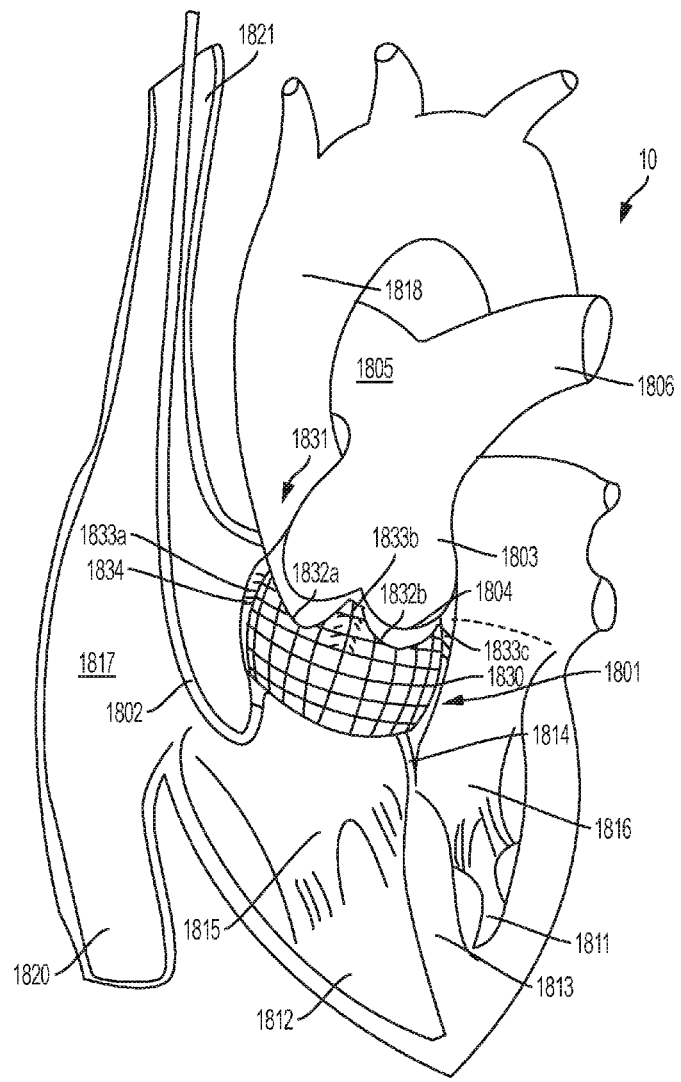
FIG. 18 shows a schematic view of an embodiment of the invention, wherein the device is arranged in the right ventricular outflow tract of the heart.

FIG. 18 shows a schematic view wherein a device according to the invention is arranged in the right ventricular outflow tract of the heart. Any device according to one of the above described embodiments can be used in the right ventricular outflow tract.

The schematic view of FIG. 18 shows a part of the heart 10 of a patient comprising the left ventricle 1811, the right ventricle 1812, the muscular portion of the interventricular septum 1813 and the membranous portion of the interventricular septum 1814. The pulmonary artery 1803, the pulmonary valve 1804, right pulmonary artery 1805, the left pulmonary artery 1806 are also shown. FIG. 18 further shows the tricuspid valve 1815, the right atrium 1817, the inferior vena cava 1820 and the superior vena cava 1821 as well as the ascending aorta 1818 and the mitral valve 1816. Approximately in the middle of FIG. 18, the root of the pulmonary artery 1803 is schematically shown together with the pulmonary valve 1804. The device 1801 is arranged in the outflow tract of the right ventricle 1812 and anchored in the sub-commissural triangles below the pulmonary valve 1804. Due to the natural pumping activity of the heart, blood is pumped from the right ventricle 1812 through the root of the pulmonary artery 1803 into the pulmonary artery. From there, the blood is further distributed into the different areas of the lung. The device 1801 can be connected by means of an electric supply line 1802 with an exterior device such as a power supply or control apparatus (not shown). In this example the electric supply line 1802 extends through the superior vena cava 1821.

FIG. 18 shows the exterior view of the holding means 1830 of the device 1801, wherein in accordance with the present embodiment, said holding means 1830 comprises a cylindrical metal frame. The first end 1831 of the metal frame 1830 is arranged adjacent to the root of the pulmonary artery 1803 and has a shape that is adapted to the anatomy of the root. Preferably, this shape can be adapted individually to the shape and size of the individual parts of the root of the pulmonary artery of a patient. In the present example, the edge of the first end 1831 has three concave recesses, wherein only two of these recesses 1832a, 1832b are shown in this view. In the area of the recesses, the mesh frame 1830 has a shorter length. Between two recesses, a respective projection 1833a, 1833b, 1833c is formed. At each projection several hooks 1834 are provided. As regards the further features reference is made to the above description of the embodiments with reference to the device implanted in the left ventricle.

Figure 19:
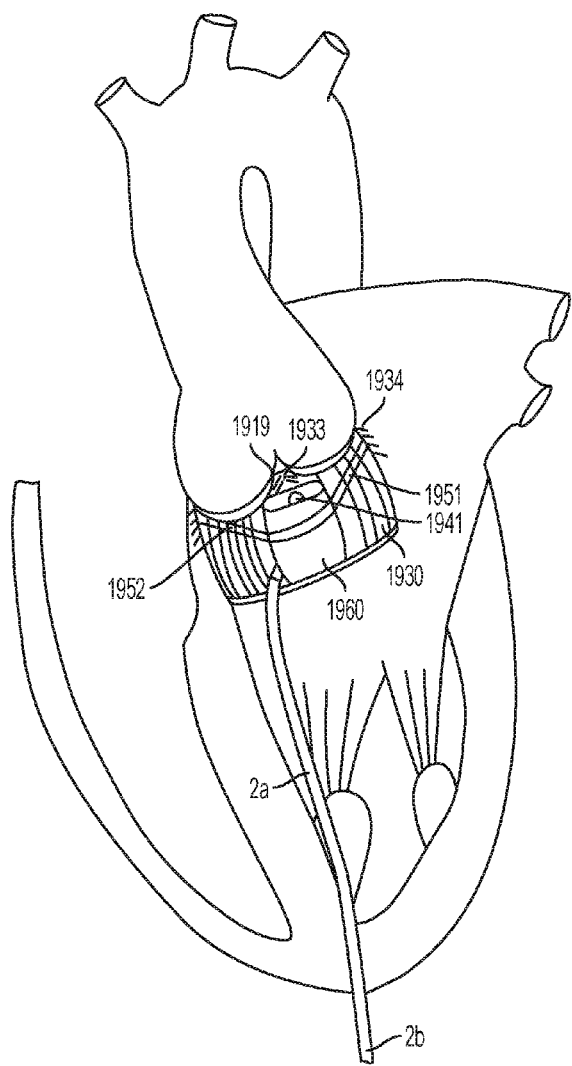
FIG. 19 shows a schematic view of an embodiment of the invention, where a small rotary pump, for example an axial flow pump or a centrifugal pump, is secured to the left ventricular outflow tract of the heart.

FIG. 19 shows a schematic view of another embodiment of the invention. As regards the anatomy and the arrangement of the holding means reference is made to the above description in particular with reference to FIGS. 1 to 4. In this embodiment a small rotary blood pump 1960, for example an axial flow pump or a centrifugal pump, is arranged in the same position as in FIGS. 1 to 4 in the sub-valvular position of the left ventricular outflow tract adjacent to the aortic valve 1919. The holding means is a stent or a stented graft 1930 comprising several hooks 1934 at each respective projection 1933 of the stent 1930. In this embodiment the stent 1930 comprises two radial holding arms 1951 and 1952 being attached at a first end of the stent and extending in an inclined manner to the second end of the stent. There can be one, two, three or more holding arms. The pump 1960 is secured in place and attached to the stent 1930 by the holding arms 1951 and 1952 in a similar manner as the pump in FIGS. 3 and 4. Reference numeral 1941 depicts the central rotor or impeller, which can be held in place by conventional pencil tip bearings or by magnetically levitated bearings. The rotary pump 1960 is connected with a driveline. In FIG. 19 the intraventricular portion 2a and a part of the extracardiac portion 2b of the driveline is shown. This rotary blood pump 1960 aspirates the blood from the left ventricular cavity and ejects the blood across the aortic valve into the systemic arterial circulation. Alternatively or additionally a similar small rotary blood pump can also be attached to a stent holding the pump in the right ventricular outflow tract.

Although the invention has been illustrated and described in detail on the basis of the Figures and the corresponding description, this illustration and this detailed description should be understood as being illustrative and exemplarily and not as limiting the invention. It is a matter of fact that experts can make changes and modifications without leaving the scope and gist of the following claims. In particular, the invention also comprises embodiments with any combination of features which are mentioned or shown above or below in connection with different embodiments.

The invention also comprises individual features in the Figures, even if they are shown therein in connection with other features and/or have not been mentioned above or below. Moreover, the alternatives of embodiments described in the Figures and in the description and individual alternatives and the features thereof might be excluded from the subject-matter of the invention and/or from the disclosed subject-matter. The disclosure comprises embodiments which comprise exclusively the features described in the claims and/or in the embodiments and also embodiments which additionally comprise other features.

I claim:

1. A device for circulatory support of a heart, comprising:
   an expandable frame configured to be implanted intracardially in a left or a right ventricular outflow tract of the heart and fixedly anchored in three subcommissural triangles underneath an aortic valve or a pulmonary valve, on a ventricular side of the aortic valve or the pulmonary valve, respectively,
   a pump disposed in the expandable frame.

2. The device according to claim 1, wherein the expandable frame comprises at least one expandable stent, wherein the stent is configured to be expanded by one of a balloon and a self-expanding force.

3. The device according to claim 2, wherein the at least one expandable stent comprises at least one hook.

4. The device according to claim 2, wherein the pump comprises an electric motor.

5. The device according to claim 4, wherein the electric motor comprises a collapsible stator and rotor.

6. The device according to claim 4, wherein the electric motor is configured to be connected to an external power supply.

* * * * *